United States Patent
Khaleghimeybodi et al.

(10) Patent No.: US 11,250,675 B2
(45) Date of Patent: Feb. 15, 2022

(54) SYSTEMS AND METHODS FOR CHARACTERIZATION OF MECHANICAL IMPEDANCE OF BIOLOGICAL TISSUES

(71) Applicant: Facebook Technologies, LLC, Menlo Park, CA (US)

(72) Inventors: Morteza Khaleghimeybodi, Bothell, WA (US); Chuming Zhao, Redmond, WA (US); Scott Porter, Woodinville, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/992,077

(22) Filed: Aug. 12, 2020

(65) Prior Publication Data
US 2021/0065523 A1 Mar. 4, 2021

Related U.S. Application Data

(60) Provisional application No. 62/895,371, filed on Sep. 3, 2019, provisional application No. 62/909,558, filed on Oct. 2, 2019.

(51) Int. Cl.
*H04B 3/36* (2006.01)
*G08B 6/00* (2006.01)

(52) U.S. Cl.
CPC ..................... *G08B 6/00* (2013.01)

(58) Field of Classification Search
CPC ...... G08B 6/00; H04R 2460/13; A61B 5/126; A61B 5/6803; A61B 5/0057; A61B 5/0051
See application file for complete search history.

(56) References Cited

U.S. PATENT DOCUMENTS

| 3,425,265 A | 2/1969 | Schloss |
| 5,549,544 A * | 8/1996 | Young ............... A61N 7/00 601/2 |
| 7,435,232 B2 | 10/2008 | Liebschner |
| 8,789,423 B2 * | 7/2014 | Rogers ............ G01M 7/027 73/663 |

(Continued)

OTHER PUBLICATIONS

International Search Report and Written Opinion on PCT/US2020/048940 on non-Foley case related to U.S. Appl. No. 16/992,077 dated Nov. 27, 2020 (12 pages).

(Continued)

*Primary Examiner* — Toan N Pham
(74) *Attorney, Agent, or Firm* — Foley & Lardner LLP

(57) ABSTRACT

A sensor system includes an actuator, an accelerometer coupled with the actuator, a rigid member, a transducer, and one or more processors. The actuator generates motion. The accelerometer outputs an acceleration signal responsive to at least the motion of the actuator. The rigid member extends from a first end coupled with the accelerometer to a second end. The transducer is coupled with the second end of the rigid member. The transducer can be configured to couple with a load, and can output a force signal responsive to at least a portion of the motion of the actuator transmitted to the transducer via the rigid member. The one or more processors determine a mechanical impedance of the load based at least on the acceleration signal and the force signal.

20 Claims, 9 Drawing Sheets

(56) References Cited

U.S. PATENT DOCUMENTS 10,726,683 B1 * 7/2020 Marchais ................ B06B 1/04
2011/0301441 A1 * 12/2011 Bandic ................ A61B 5/0059
600/306

OTHER PUBLICATIONS

Scott, D.A. et al: "Traceable Calibration of Impedance Heads and Artificial Mastoids", Measurement Science and Technology IOP, Bristol, BG vol. 26, No. 12 Nov. 12, 2015, p. 125013 (10 pages total).

* cited by examiner

SYSTEMS AND METHODS FOR CHARACTERIZATION OF MECHANICAL IMPEDANCE OF BIOLOGICAL TISSUES

CROSS-REFERENCE TO RELATED APPLICATIONS

The present disclosure claims the benefit of and priority to U.S. Provisional Application No. 62/895,371, titled "SYSTEMS AND METHODS FOR CHARACTERIZATION OF MECHANICAL IMPEDANCE OF BIOLOGICAL TISSUES," filed Sep. 3, 2019, and U.S. Provisional Application No. 62/909,558, titled "SYSTEMS AND METHODS FOR CHARACTERIZATION OF MECHANICAL IMPEDANCE OF BIOLOGICAL TISSUES," filed Oct. 2, 2019, the disclosures of which are incorporated herein by reference in their entireties.

FIELD OF THE DISCLOSURE

The present disclosure relates generally to sensor systems. More particularly, the present disclosure relates to systems and methods for characterization of mechanical impedance of biological tissues.

BACKGROUND

The present disclosure relates generally to sensor systems, such as sensor systems that can be used to measure mechanical impedance of loads. Mechanical impedance can correspond to a complex ratio of dynamic force to the resulting velocity of loads. Mechanical impedance can be associated with a response of the load to being driven at a frequency, such as for audio or haptic content delivery.

SUMMARY

Various aspects of the present disclosure relate to systems and methods for characterizing the mechanical impedance of biological tissues, such as to determine relationships between outputs that are generated by audio or haptic devices and the response of the biological tissue to the outputs. For example, a sensor can be used to detect the mechanical impedance of lightweight structures, such as biological tissues, that might otherwise have less mass than one or more components of the system. The sensor can be integrated into wearable devices, including haptic devices or audio delivery devices. The sensor can be used to tune properties of transducers and coupling mechanisms in cartilage conduction and bone conduction, such as to improve the transfer of energy.

The sensor can include a high-bandwidth shaker, an accelerometer, a stinger, and a transducer. The high-bandwidth shaker can operate as an actuator to cause the accelerometer, stinger, and transducer to move based on how the shaker is controlled. For example, the shaker can cause oscillation of the other components in a frequency range of interest for measurement, such as 20 Hz to 20 kHz (e.g., human hearing range). The transducer can contact a structure for which the mechanical impedance is to be measured.

The accelerometer can output acceleration data responsive to being driven by the shaker, and the acceleration data can be integrated over time to generate velocity data. The stinger can be a rigid element, such as an aluminum, steel, or 3D printed member, that meets sufficient rigidity requirements over the frequency range of interest so that forces generated by the shaker are transferred to the transducer.

The transducer can output force data, so that the mechanical impedance can be calculated based on the acceleration data (e.g., velocity data generated from the acceleration data) and the force data. The transducer can have a relatively low mass (e.g., less than 300 mg), which can enable the sensor to have sufficient sensitivity and accuracy to quantify the mechanical impedance of lightweight subjects, such as biological tissues.

The sensor can be calibrated based on experimentally measured data to generate a relationship (e.g., transfer function) relating a voltage outputted by the transducer to the vibration excitation (e.g., voltage divided by velocity as a function of shaker frequency). A model, such as a finite element analysis (FEA) model, can also be used to define relationships between the input to the system and the resulting behavior of the load. For example, the FEA model can be based on size parameters of the transducer with known material properties. The model can simulate the system behavior as the transfer function (voltage divided by velocity over frequency), which can have decreasing transfer function response with a slope proportional to $-1/\text{frequency}$ at relatively low frequencies caused by stiffness of the load (e.g., spring-like behavior of the load), a constant or flat transfer function response at middle frequencies caused by a dashpot/damping, and a rising transfer function response with a slope proportional to the frequency at relatively high frequencies (e.g., frequencies above the resonant frequency). Various models, including machine learning models, may be used that take into account additional variables, such as temperature and hydration, to characterize the system and determine the response of the load to the input provided.

The mechanical impedance can be used to establish a baseline, which can then be personalized to various users based on data measured over time or in real time. The mechanical impedance can be used to detect whether a device is expected to be operational (e.g., in contact with biological tissue), such as to turn off power based on detecting that the device is not in use. The mechanical impedance can be used to confirm that the transducer is seated properly, to monitor fit-to-fit differences across device usage or users, and to generate user profiles for the relationship between mechanical impedance and the frequency at which the device is driven. The data monitored regarding users, including mechanical impedance data, can be monitored responsive to receiving user consent. The transducer can be used as both an actuator and a sensor; for example, it can be used as an actuator at high frequencies to supplement other low-frequency drivers, enabling more effective tuning of the capacitors that drive the system. The mechanical impedance can be used to generate training data for training and updating the model(s), which may be further labeled based on user feedback.

At least one aspect relates to a sensor system. The sensor system can include an actuator that generates motion. The sensor system can include an accelerometer coupled with the actuator. The accelerometer can output an acceleration signal responsive to at least the motion of the actuator. The sensor system can include a rigid member extending from a first end coupled with the accelerometer to a second end. The sensor system can include a transducer coupled with the second end of the rigid member. The transducer can be configured to couple with a load, and can output a force signal responsive to at least a portion of the motion of the actuator transmitted to the transducer via the rigid member. The sensor system can include one or more processors that determine a mechanical impedance of the load based at least on the acceleration signal and the force signal.

At least one aspect relates to a method. The method can include coupling a sensor with a load. The method can include driving an actuator of the sensor at a target frequency. The method can include receiving an acceleration signal from an accelerometer of the sensor. The method can include receiving a force signal from a transducer of the sensor. The method can include determining, by one or more processors, a mechanical impedance of the load using the acceleration signal and the force signal.

At least one aspect relates to a sensor. The sensor can include an accelerometer coupled with the actuator. The accelerometer can output an acceleration signal responsive to at least the motion of the actuator. The sensor can include a rigid member extending from a first end coupled with the accelerometer to a second end. The sensor can include a transducer coupled with the second end of the rigid member. The transducer can be configured to couple with a load, and can output a force signal responsive to at least a portion of the motion of the actuator transmitted to the transducer via the rigid member.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings.

DETAILED DESCRIPTION

Figure 1:
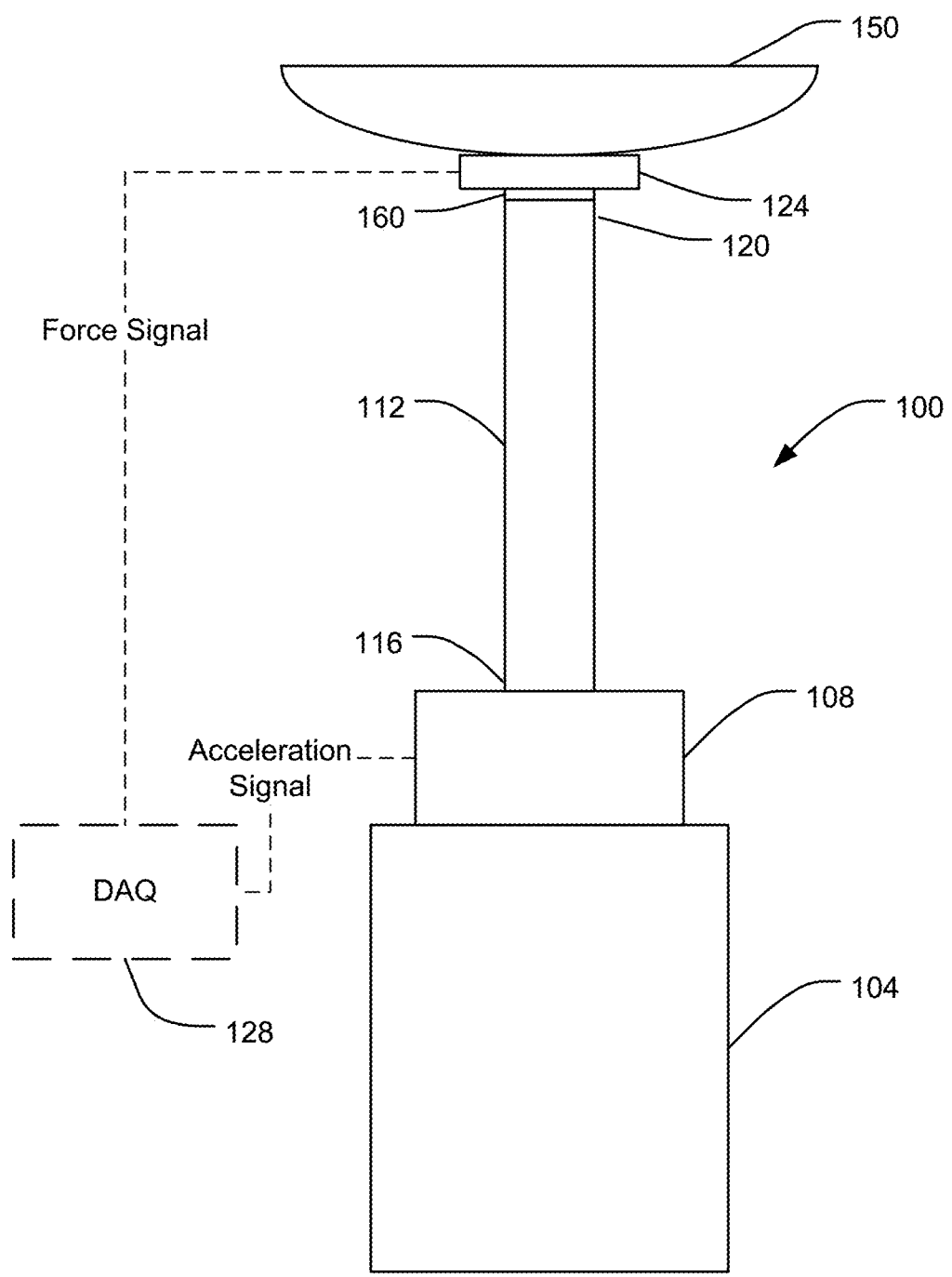
FIG. 1 is a schematic diagram of a sensor that can be used to detect mechanical impedance according to an implementation of the present disclosure.

Before turning to the figures, which illustrate certain embodiments in detail, it should be understood that the present disclosure is not limited to the details or methodology set forth in the description or illustrated in the figures. It should also be understood that the terminology used herein is for the purpose of description only and should not be regarded as limiting.

Various devices may provide output that includes audio or haptic output to a user. For example, wearable devices, including HMDs, may provide such output via direct or indirect contact with skin, cartilage, or bone of the user (or using a combination of some of these). The devices may be associated or form part of an augmented reality (AR) or virtual reality (VR) system. For example, content delivered by such systems may include image, video, audio, or haptic output, or any combination thereof, any of which may be presented in one or more channels.

AR and VR systems can use an HMD (may also be referred to as a head-worn display (HWD)) to present images to a user to represent an augmented or virtual environment (e.g., simulated environment). The HMD can present the images so that the images are perceived with realistic depth. For example, the HMD can be used to present images that can be viewed stereoscopically, such as by sequentially or simultaneously presenting left eye images and right eye images, enabling a user to perceive a 3D environment. An AR system can present images using an at least partially transparent display, enabling the presented images to be perceived together with a real-world environment. A VR system can generate the images based on operating an application that generates display data regarding the virtual environment, and updates the display data responsive to interactions of the user with the virtual environment. The AR or VR system can include the HMD (e.g., headset), which can be worn by the user to present the display data to the user, as well as one or more hand devices, such as hand-held controllers, that can be manipulated by the user as the user interacts with the virtual environment. The AR or VR system can use any of a variety of audio and haptic output devices, such as transducers, speakers, and other movable members, to provide audio or haptic output together with or independently from images.

The mechanical impedance ($Z_{mech}$) of a structure can be defined as a ratio of a dynamic force applied to the structure (F) to a resulting velocity of the structure (v). An impedance head sensor can be used to measure the mechanical impedance. However, impedance head sensors may have difficulty or be unable to measure the mechanical impedance of lightweight structures and loads, including biological tissues such as those associated with fingers, wrists, ears, or auricular cartilage. These tissues may be useful for providing audio or haptic output to a user, but the quality of this output may be limited without effective measurement of their mechanical impedance. In some cases, the ability of the impedance head sensor to measure the mechanical impedance may be limited by a mass of a force sensor (or a mass added above the force sensor) used in the impedance head sensor to measure the force applied to the load relative to a mass of the load; for example, the measured impedance at frequencies above a resonant frequency of the system may be covered with the impedance of the internal mass of the sensor, such that the mechanical impedance of the load cannot be measured. For example, regardless of the mass of the load, the measured impedances as a function of applied frequency may converge to a same value once the applied frequency becomes greater than the resonant frequency of the respective load. This may be the case with biological tissues and other loads having resonant frequencies in the range of 10 Hz to 1 kHz, while the audio or haptic output to be provided may have an expected frequency greater than 10 KHz (e.g., as high as 20 kHz).

Systems and methods in accordance with certain aspects of the present solution can more effectively measure mechanical impedance of loads such as biological tissues, including at frequencies above a resonant frequency of the loads, enabling improved perception of the audio or haptic content being delivered to a user. For example, a sensor can include a high-bandwidth shaker, an accelerometer, a stinger, and a transducer. The high-bandwidth shaker can operate as an actuator to cause the accelerometer, stinger, and transducer to move based on how the shaker is controlled. For example, the shaker can cause oscillation of the other components in a frequency range of interest for measurement, such as 20 Hz to 20 kHz (e.g., human hearing range). The transducer can contact a structure for which the mechanical impedance is to be measured. Although the present disclosure will be presented in connection with measuring mechanical impedance of biological tissues, the principles can be extended to measuring mechanical impedance of other lightweight structures, including non-biological structures.

The accelerometer can output acceleration data responsive to being driven by the shaker, and the acceleration data can be integrated over time to generate velocity data. The stinger can be a rigid element, such as an aluminum, steel, or 3D printed member, that meets sufficient rigidity requirements over the frequency range of interest so that forces generated by the shaker are transferred to the transducer.

The transducer can output force data, so that the mechanical impedance can be calculated based on the acceleration data (e.g., velocity data generated from the acceleration data) and the force data. The transducer can have a relatively low mass (e.g., less than 0.5 g), which can enable the sensor to have sufficient sensitivity to detect the mechanical impedance of biological tissues. The transducer can apply a preload (e.g., static load) to the load, which can be adjusted to maintain the preload within a threshold of a target value, such as to enable effective bone conduction or cartilage conduction.

The sensor can be calibrated based on experimentally measured data to generate a relationship (e.g., transfer function) relating a voltage outputted by the transducer to the force sensitivity of the sensor (e.g., voltage divided by velocity as a function of shaker frequency). A model, such as a finite element analysis (FEA) model, can also be used to define relationships between the input to the system and the resulting behavior of the load. For example, the FEA model can be based on size parameters of the transducer with known material properties. The model can simulate system behavior based on a spring constant of the stinger causing voltage to decrease with frequency at low frequencies, a dashpot/damping constant causing voltage to be constant with frequency at middle frequencies, and a mass of the sensor causing voltage to increase with frequency at high frequencies. Various models, including machine learning models, may be used that take into account additional variables, such as temperature and hydration, to characterize the system and determine the response of the load to the input provided.

The mechanical impedance can be used to establish a baseline, which can then be personalized to various users based on data measured over time. The mechanical impedance can be used to detect whether a device is expected to be operational (e.g., in contact with biological tissue), such as to turn off power based on detecting that the device is not in use. The mechanical impedance can be used to confirm that the transducer is seated properly, to monitor fit-to-fit differences across device usage or users, and to generate user profiles for the relationship between mechanical impedance and the frequency at which the device is driven. The device can be used as both an actuator and a sensor; for example, it can be used as an actuator at high frequencies to supplement other low-frequency drivers, enabling more effective tuning of the capacitors that drive the system. The mechanical impedance can be used to generate training data for training and updating the model(s), which may be further labeled based on user feedback.

Referring now to FIG. 1, a sensor 100 can include an actuator 104. The actuator 104 can move at a frequency based on a control signal provided to the actuator 104. For example, the actuator 104 can oscillate at the frequency. The actuator 104 can be a shaker, such as a high bandwidth shaker that can be driven at frequencies across a relatively large bandwidth. The actuator 104 can move at a frequency within a frequency range that at least partially overlaps a human hearing range. For example, the actuator 104 can move at a frequency greater than or equal to 10 Hz and less than or equal to 40 kHz. The actuator 104 can move at a frequency greater than or equal to 20 Hz and less than or equal to 20 kHz.

The sensor 100 includes an accelerometer 108 coupled with the actuator 104. The accelerometer 108 can be attached to the actuator 104. The accelerometer 108 can output an acceleration signal, which can indicate an acceleration of the accelerometer 108 responsive to motion of the actuator 104. The accelerometer 108 can output the acceleration signal periodically, responsive to receiving a request for the acceleration signal, responsive to the acceleration being greater than a threshold acceleration, or any combination thereof. The accelerometer 108 can generate the acceleration signal to indicate the acceleration. The accelerometer 108 can generate the acceleration signal to indicate velocity (e.g., by integrating acceleration data as a function of time), or a device that receives the acceleration signal can use the acceleration indicated by the acceleration signal to determine velocity.

The sensor 100 includes a rigid member 112 that extends from a first end 116 coupled with the accelerometer 108 to a second end 120. The rigid member 112 can have a sufficient rigidity to transmit at least a threshold fraction of movement caused by the actuator 104 to a transducer 124. The rigid member 112 can be a stinger. The rigid member 112 can be made from materials such as aluminum or steel. The rigid member 112 can be manufactured through additive manufacturing (e.g., three-dimensional printing). For example, the rigid member 112 can be manufactured to have relatively thick walls as compared to a core region. The rigid member 112 can be a composite.

The rigidity of the rigid member 112 can be defined based on stiffness of the rigid member 112 responsive to receiving a force at a frequency at which the sensor 100 is operated or expected to be operated. For example, the rigidity can be defined based on force applied to the rigid member 112 relative to deformation of the rigid member 112 (e.g., expressed in Newtons/meter) at a frequency within a frequency range that at least partially overlaps human hearing range, such as a frequency greater than or equal to 10 Hz and less than or equal to 40 kHz or greater than or equal to 20 Hz and less than or equal to 20 kHz. The rigidity of the rigid member 112 may be greater than a threshold rigidity under these conditions, such as a threshold rigidity of at least 1500 N/m.

The transducer 124 can be coupled with the second end 116 of the rigid member 112. For example, the transducer 124 can be attached to the second end 116 of the rigid member 112. The transducer 124 can move responsive to movement of the rigid member 112 (e.g., as caused by the actuator 104). The transducer 124 can contact a load 150, such that a force associated with movement caused by the actuator 104 is transferred to the load 150 via the transducer 124. The transducer 124 can include a diaphragm or movable member that can move or change in shape responsive to one or more forces applied to the transducer 124.

The transducer 124 can output a force signal representing a response of the load 150 to the force transferred to the load 150. The force signal can correspond with the acceleration signal outputted by the accelerometer, so that the mechanical impedance of the load 150 can be determined using the force signal and the acceleration signal. For example, a force value indicated by or determined based on the force signal can be divided by a velocity value indicated by or determined based on the acceleration signal to determine the mechanical impedance. The transducer 124 can be a piezoelectric transducer, which can output an electrical signal having a voltage representative of the force associated with the load 150 (e.g., due to compression of the transducer 124 between the load 150 and the rigid member 112). Other transducers may be used which provide similar outputs based on detected force. The sensor 100 can include a preamplifier (e.g., junction gate field-effect transistor (JFET) preamplifier) that buffers the electric signal from the piezoelectric transducer (e.g., an AC component as discussed below).

The force signal representing the response of the load 150 can include a DC component and an AC component. For example, where the transducer 124 is implemented using a piezoelectric transducer, the transducer 124 can detect the AC component and output an AC force signal representative of the AC component, and the sensor 100 can include a force sensor 160 that detects the DC component and outputs a DC force signal representative of the DC component. The force sensor 160 can be between the transducer 124 and the second end 120 of the rigid member 112, such as by being laminated between the transducer 124 and the rigid member 112. The sensor 100 can use the DC force signal to keep good contact between the rigid member 112 and the load 150, such as based on a preload applied by the transducer 124 based on the DC force signal.

The transducer 124 can directly or indirectly contact the load 150, while maintaining a relatively low internal mass so that the mechanical impedance of the load 150 can be measured even when the actuator 104 operates at frequencies greater than a resonant frequency of the load 150.

The transducer 124 can apply a preload to the load 150. The preload may represent a static load applied to the load 150. The preload can be controlled for various purposes, such as to enable the sensor 100 to establish a preload that is effective for particular applications, such as bone conduction or cartilage conduction. The sensor 100 can include the force sensor 160 to measure the preload. For example, the force sensor 160 can be positioned between the transducer 124 and the load 150 to measure the preload.

The sensor 100 can include a spring that can be coupled to the load 150. The spring can be used to adjust the preload applied to the load 150. For example, a length or shape of the spring can be adjusted (e.g., using an actuator coupled to the spring) to cause a resulting change in a spring force applied by the spring to the load 150, such as to adjust the preload. The spring can include a flexible material, or a shape memory material, such as nitinol, such that the spring force can be applied based on temperature or other parameters of the shape memory material.

The sensor 100 can maintain the preload at or within a threshold of a target value. For example, the sensor 100 (e.g., using processing circuitry 616 described with reference to FIG. 6) can receive the preload measured by the force sensor 160, compare the preload to a target value (e.g., target DC force value), and adjust the spring based on the comparison to reduce a difference between the preload and the target value, such as to reduce the difference between the preload and the target value to less than a threshold difference. The target DC force value can be greater than or equal to 0.25 Newtons and less than or equal to 1 Newton. The sensor 100 can select the target value based on a mode of operation. For example, the sensor 100 can receive an indication that the mode of operation includes performing bone conduction or performing cartilage conduction, and can select the target value based on the received indication. The sensor 100 can use the spring to maintain the preload within the threshold of the target value while using the transducer 124 and accelerometer 108 to measure parameters for determining the mechanical impedance.

Figure 2:
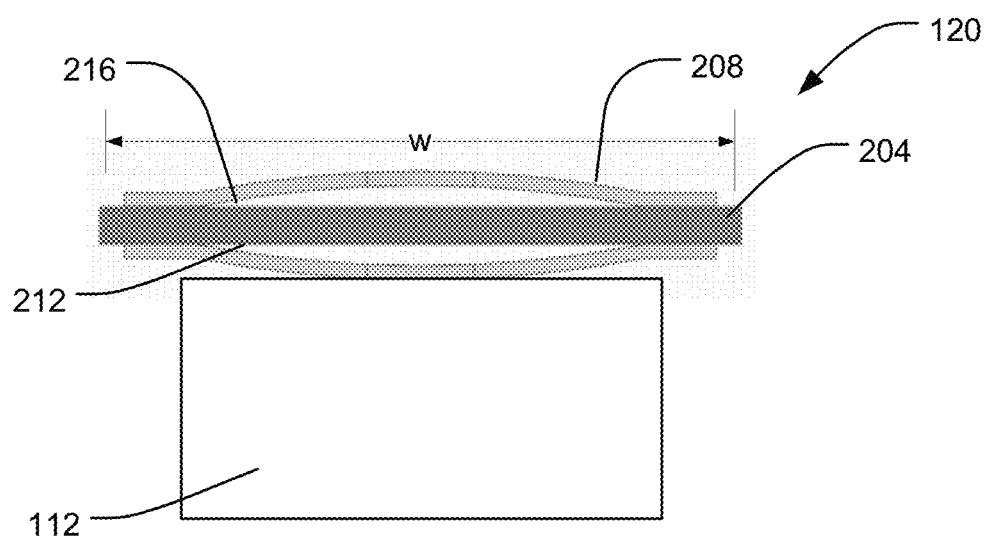
FIG. 2 is a schematic diagram of a transducer used to detect mechanical impedance according to an implementation of the present disclosure.

As depicted in FIG. 2, the transducer 124 can include at least one piezoelectric layer 204, which can be coupled with at least one bracket 208. The at least one piezoelectric layer 204 may include a stack of piezoelectric layers 204. The at least one bracket 208 can be provided on at least one of a first side 212 of the at least one piezoelectric layer 204 (e.g., the first side 212 facing the rigid member 212) or a second side 216 of the at least one piezoelectric layer 204 (e.g., the second side 216 that may face towards or contact the load 150). For example, a first bracket 208 can be provided on the second side 216 but not the first side 212, such that the rigid member 112 directly contacts the at least one piezoelectric layer 204. The at least one bracket 208 can have a width less than a width w of the at least one piezoelectric layer 204.

The at least one piezoelectric layer 204 (and at least one bracket 208) can be sized to have an internal mass comparable to or less than an expected internal mass of the load 150, which can enable the transducer 124 to detect force data for determining the mechanical impedance under a variety of conditions (e.g., for lightweight biological tissue structures). For example, the internal mass can be less than or equal to 10 grams (g). The internal mass can be less than or equal to 8 g. The internal mass can be less than or equal to 5 g. The internal mass can be less than or equal to 2.5 g. The internal mass can be less than or equal to 1 g. The internal mass can be less than or equal to 0.5 g. The internal mass can be less than or equal to 0.25 g. The width w can be less than or equal to 20 millimeters (mm). The width w can be less than or equal to 15 mm. The width w can be less than or equal to 12 mm. The width w can be less than or equal to 10 mm. The width w can be less than or equal to 8 mm. The width w can be less than or equal to 5 mm. The width w can be less than or equal to 3 mm. The width w can be less than or equal to 1 mm.

Figure 3:
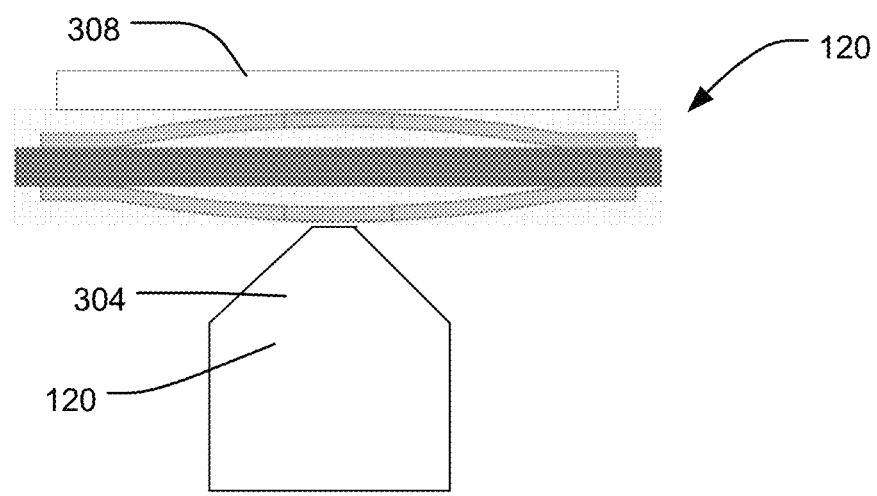
FIG. 3 is a schematic diagram of a transducer and a rigid member having a tip according to an implementation of the present disclosure.

As depicted in FIG. 3, the rigid member 112 can have a tip 304 at the second end 120. The tip 304 can decrease in width in a direction from the first end 116 towards the second end 120. As such, the rigid member 112 can have a relatively reduced size while maintaining the ability to transfer forces to the transducer 124.

Figure 4:
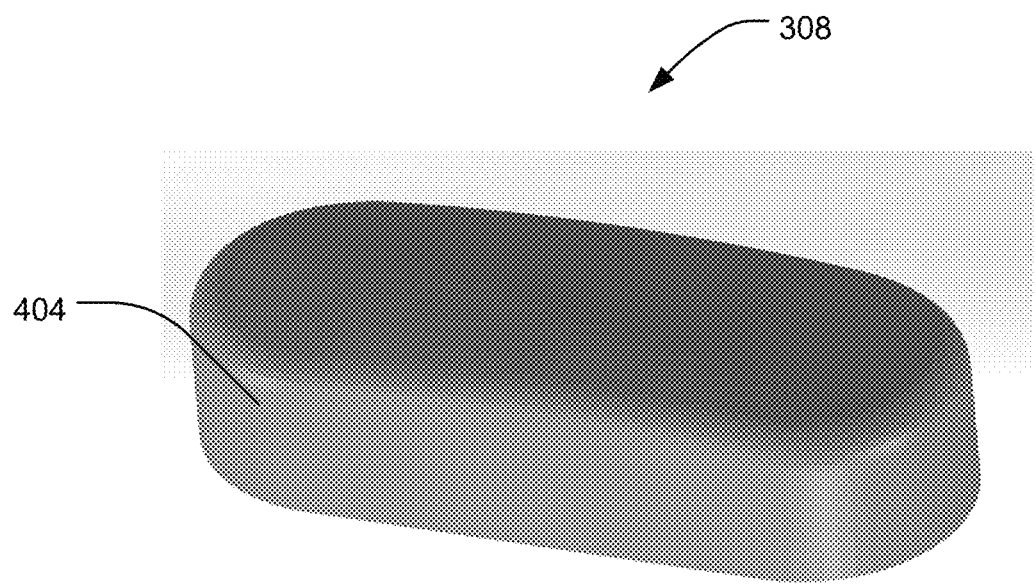
FIG. 4 is a front perspective view of a pad of a sensor used to detect mechanical impedance according to an embodiment of the present disclosure.
Figure 5:
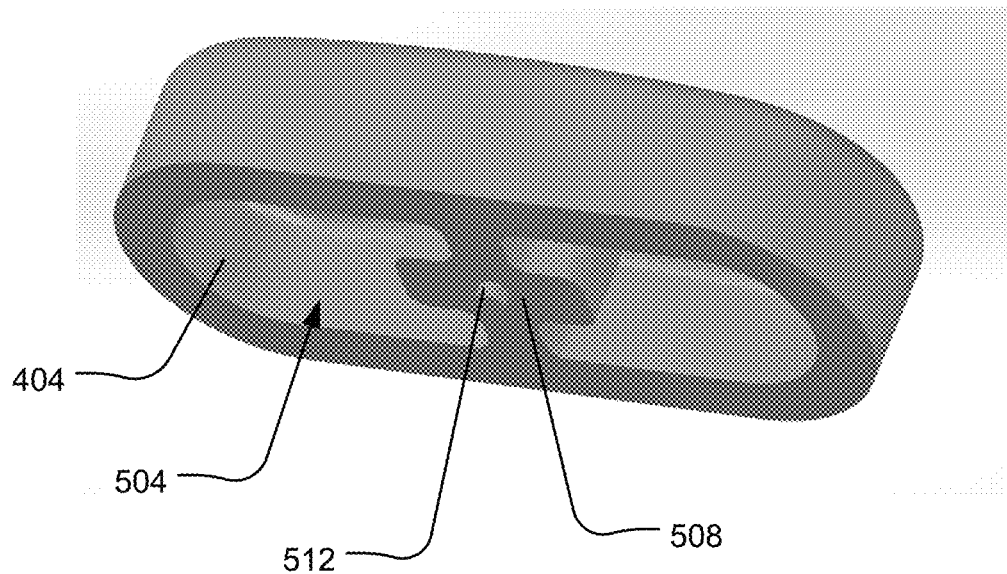
FIG. 5 is a rear perspective view of a pad of a sensor used to detect mechanical impedance according to an embodiment of the present disclosure.

As depicted in FIGS. 3-5, a pad 308 can be provided on the second side 216 of the at least one piezoelectric layer 204. The pad 308 can enable the sensor 100 to have improved control over the contact area between the sensor 100 and the load 150 in order to transmit forces between the at least one piezoelectric layer 204 and the load 150. The pad 308 can be adjacent to the bracket 208. The pad 308 can have a width less than the width of the at least one piezoelectric layer 204.

The pad 308 can be shaped to have a relatively reduced mass while functioning to transmit forces between the at least one piezoelectric layer 204 and the load 150. For example, the pad 308 can define one or more internal spaces 504 between a sidewall 404 and a center wall 508. The center wall 508 can include an extension 512 to facilitate contact with and alignment with the at least one piezoelectric layer 204 or the bracket 208.

Referring further to FIG. 1, the sensor 100 can include or be connected with a data acquisition unit 128, which can receive the force signal and the acceleration signal. The data acquisition unit 128 can be implemented by or communicate with (e.g., via wired or wireless connection) one or more features of system 600 described with reference to FIG. 6 below. For example, the data acquisition unit 128 can request or periodically receive the force signal and the acceleration signal from the transducer 124 and accelerometer 108, respectively. In some implementations, the data acquisition unit 128 determines the mechanical impedance using the force signal and the acceleration signal.

Figure 6:
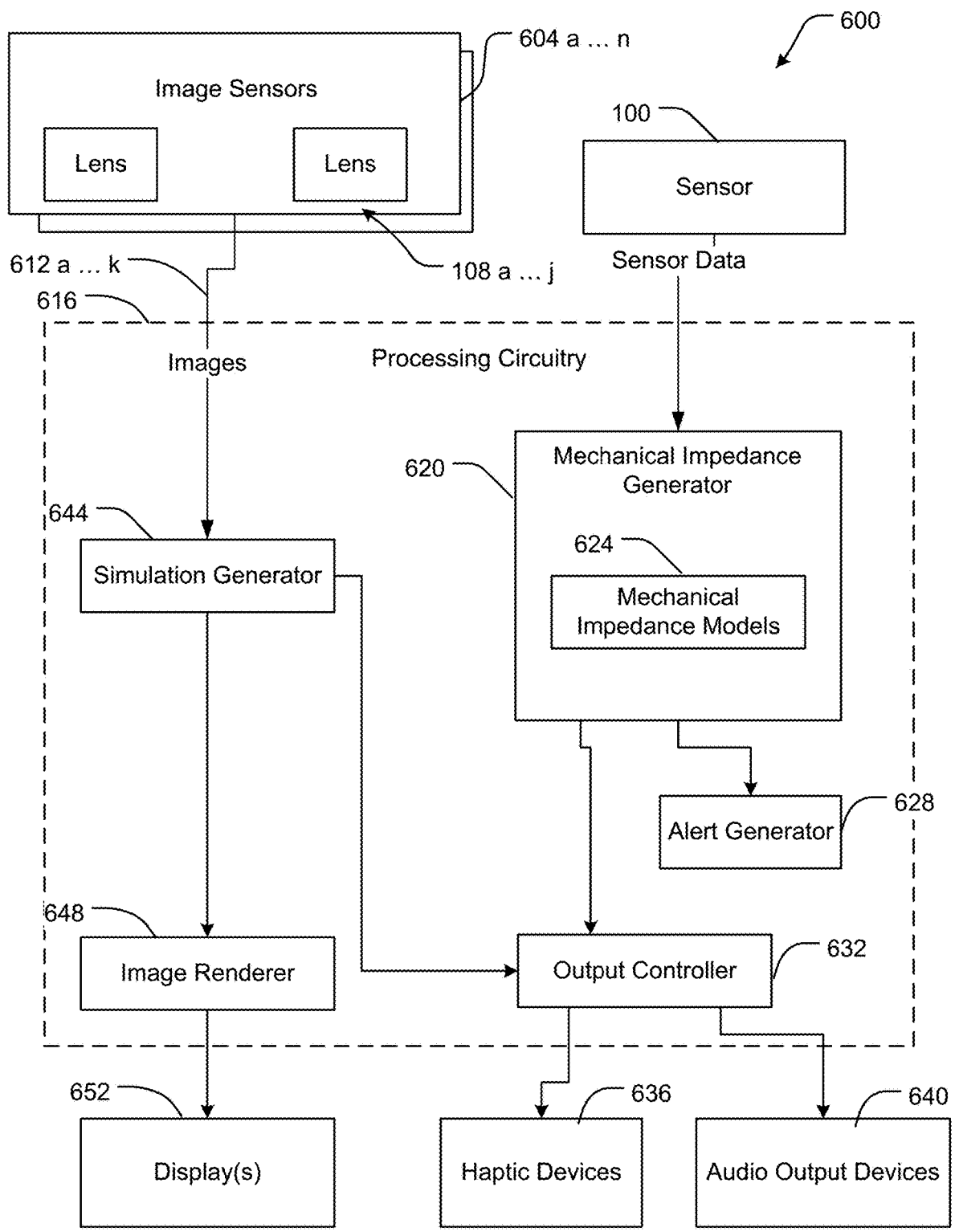
FIG. 6 is a block diagram of an augmented reality/virtual reality (AR/VR) system according to an implementation of the present disclosure.

Referring now to FIG. 6, a system 600 can be used to perform various processes on the data generated by the sensor 100, such as to determine the mechanical impedance of the load 150 using the force signal and the acceleration signal. While the system 600 is depicted in FIG. 6 as performing such operations along with an image processing pipeline, various aspects of the system 600 may or may not be performed together with image processing operations.

The system 600 can include a plurality of sensors 604a . . . n, processing circuitry 616, and one or more displays 652. The system 600 can be implemented using the HMD system 700 described with reference to FIG. 7, the headset 800 described with reference to FIG. 8, the audio system 900 described with reference to FIG. 900, the computing environment described with reference to FIG. 11, or any combination thereof. The system 600 can incorporate features of and be used to implement features of AR and VR systems. At least some of the processing circuitry 616 can be implemented using a graphics processing unit (GPU). The functions of the processing circuitry 616 can be executed in a distributed manner using a plurality of processing units.

The processing circuitry 616 may include one or more circuits, processors, and/or hardware components. The processing circuitry 616 may implement any logic, functions or instructions to perform any of the operations described herein. The processing circuitry 616 can include any type and form of executable instructions executable by any of the circuits, processors or hardware components. The executable instructions may be of any type including applications, programs, services, tasks, scripts, libraries processes and/or firmware. Any of the components of the processing circuitry 616 including but not limited to the mechanical impedance generator 620, alert generator 628, output controller 632, simulation generator 644, and image renderer 648 may be any combination or arrangement of hardware, circuitry and executable instructions to perform their respective functions and operations. At least some portions of the processing circuitry 616 can be used to implement image processing executed by the sensors 604.

The sensors 604a . . . n can be image capture devices or cameras, including video cameras. The sensors 604a . . . n may be cameras that generate images of relatively low quality (e.g., relatively low sharpness, resolution, or dynamic range), which can help reduce the SWAP of the system 600. For example, the sensors 604a . . . n can generate images having resolutions on the order of hundreds of pixels by hundreds of pixels. At the same time, the processes executed by the system 600 as described herein can be used to generate display images for presentation to a user that have desired quality characteristics, including depth characteristics.

The sensors 604a . . . n (generally referred herein as sensors 604) can include any type of one or more cameras. The cameras can be visible light cameras (e.g., color or black and white), infrared cameras, or combinations thereof. The sensors 604a . . . n can each include one or more lenses 608 a . . . j generally referred herein as lens 608). In some embodiments, the sensor 604 can include a camera for each lens 608. In some embodiments, the sensor 604 include a single camera with multiple lenses 608 a . . . j. In some embodiments, the sensor 604 can include multiple cameras, each with multiple lenses 608. The one or more cameras of the sensor 604 can be selected or designed to be a predetermined resolution and/or have a predetermined field of view. In some embodiments, the one or more cameras are selected and/or designed to have a resolution and field of view for detecting and tracking objects, such as in the field of view of a HMD. The one or more cameras may be used for multiple purposes, such as tracking objects in a scene or an environment captured by the image capture devices and performing the collision detection techniques described herein.

The one or more cameras of the sensor 604 and lens 608 may be mounted, integrated, incorporated or arranged on an HMD to correspond to a left-eye view of a user or wearer of the HMD and a right-eye view of the user or wearer. For example, an HMD may include a first camera with a first lens mounted forward-facing on the left side of the HMD corresponding to or near the left eye of the wearer and a second camera with a second lens mounted forward-facing on the right-side of the HMD corresponding to or near the right eye of the wearer. The left camera and right camera may form a front-facing pair of cameras providing for stereographic image capturing. In some embodiments, the HMD may have one or more additional cameras, such as a third camera between the first and second cameras an offers towards the top of the HMD and forming a triangular shape between the first, second and third cameras. This third camera may be used for triangulation techniques in performing the depth buffer generations techniques of the present solution, as well as for object tracking.

The system 600 can include a first sensor (e.g., image capture device) 604a that includes a first lens 608a, the first sensor 604a arranged to capture a first image 612a of a first view, and a second sensor 604b that includes a second lens 608b, the second sensor 604b arranged to capture a second image 612b of a second view. The first view and the second view may correspond to different perspectives, enabling depth information to be extracted from the first image 612a and second image 612b. For example, the first view may correspond to a left eye view, and the second view may correspond to a right eye view. The system 600 can include a third sensor 604c that includes a third lens 608c, the third sensor 604c arranged to capture a third image 612c of a third view. As described with reference to FIG. 7, the third view may correspond to a top view that is spaced from an axis between the first lens 608a and the second lens 608b, which can enable the system 600 to more effectively handle depth information that may be difficult to address with the first sensor 604a and second sensor 604b, such as edges (e.g., an edge of a table) that are substantially parallel to the axis between the first lens 608a and the second lens 608b.

Light of an image to be captured by the sensors 604a . . . n can be received through the one or more lenses 608 a . . . j. The sensors 604a . . . n can include sensor circuitry, including but not limited to charge-coupled device (CCD) or complementary metal-oxide-semiconductor (CMOS) circuitry, which can detect the light received via the one or more lenses 608a . . . j and generate images 612a . . . k based on the received light. For example, the sensors 604a . . . n can use the sensor circuitry to generate the first image 612a corresponding to the first view and the second image 612b corresponding to the second view. The one or more sensors 604a . . . n can provide the images 612a . . . k to the processing circuitry 616. The one or more sensors 604a . . . n can provide the images 612a . . . k with a corresponding timestamp, which can facilitate synchronization of the images 612a . . . k when image processing is executed on the images 612a . . . k.

Figure 7:
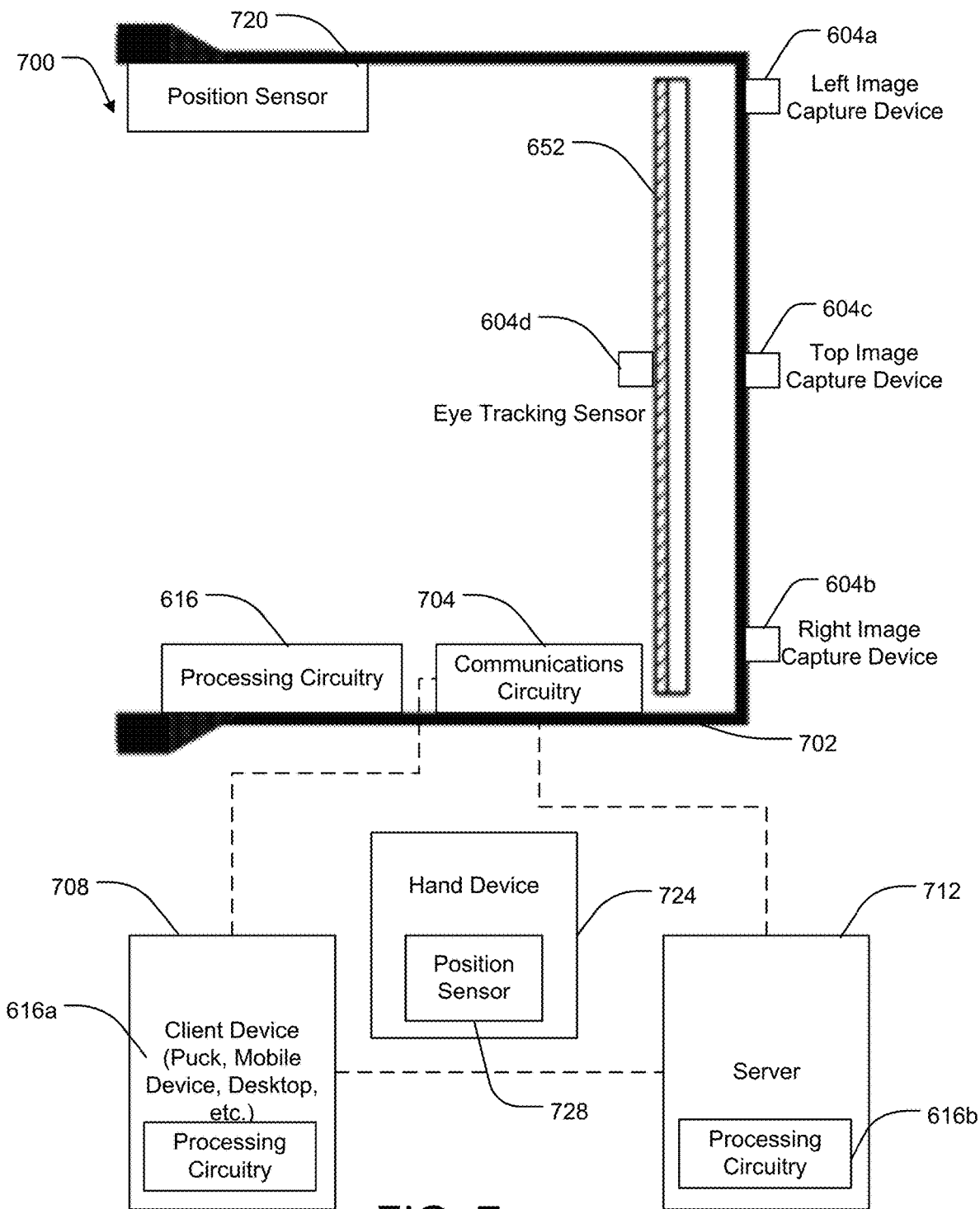
FIG. 7 is a schematic diagram of a head-mounted display (HMD) system according to an implementation of the present disclosure.

The sensors 604 can include eye tracking sensors 604 or head tracking sensors 604 that can provide information such as positions, orientations, or gaze directions of the eyes or head of the user (e.g., wearer) of an HMD. In some embodiments, the sensors 604 are inside out tracking cameras configured to provide images for head tracking operations. The sensors 604 can be eye tracking sensors 604 that provide eye tracking data, such as data corresponding to at least one of a position or an orientation of one or both eyes of the user. In some embodiments, the sensors 604 optically measure eye motion, such as by emitting light (e.g., infrared light) towards the eyes and detecting reflections of the emitted light. The sensors 604 can be oriented in a direction towards the eyes of the user (e.g., as compared to sensors 604 that capture images of an environment outside of the HMD). For example, the sensors 604 can include at least one fourth sensor 604d (e.g., as illustrated in FIG. 7) which can be oriented towards the eyes of the user to detect sensor data regarding the eyes of the user. In some embodiments, the head tracking sensors 604 generate motion data including at least one of a position, a velocity, or an acceleration of the head (e.g., of the HMD).

The sensors 604 can include hand tracking sensors 604 that can provide information such as positions or orientations of one or more hands of the user. The hand tracking sensors 604 can generate motion data including at least one of a position, a velocity, or an acceleration of a respective hand (e.g., of a hand device 724 manipulated by the hand as described with reference to FIG. 7). The head tracking sensors 704 and hand tracking sensors 704 can include any of a variety of position sensors, such as an inertial measurement unit (IMU), an accelerometer, a gyroscope, a magnetometer (e.g., magnetic compass), or any combination thereof. The sensors 704 can include various body position sensors such as leg sensors or torso sensors.

The sensors 604 can capture images 612 of an environment around the sensors 604. For example, the sensors 604 can capture images 612 of an environment in or around a field of view of the user of the HMD. The images 612 can be representations of the environment, such as color or grayscale array or matrix of pixels representing parameters of light captured from the environment (e.g., color, brightness, intensity). The environment can be an indoor or outdoor environment, including both natural and man-made structures, terrain, or other objects, including sky, clouds, roads, buildings, streets, pedestrians, or cyclists. The environment can include one or more objects (e.g., real-world objects), which can be represented by the images 612 captured by the sensors.

The processing circuitry 616 can include a mechanical impedance generator 620. The mechanical impedance generator 620 can include any function, operation, routine, logic, or instructions to perform functions such as determining the mechanical impedance of the load based on sensor data received from the sensor 100. For example, the mechanical impedance generator 620 can determine the mechanical impedance using the force signal and the acceleration signal received from the sensor 100, such as by dividing a force value of the force signal by a velocity value associated with the acceleration signal. The mechanical impedance generator 620 may receive the force value as a voltage output from the sensor 100, and convert the voltage output to the force value based on a predetermined calibration associated with the sensor 100. The mechanical impedance generator 620 may receive the acceleration signal as an acceleration value, and determine the velocity value in various manners, such as by integrating acceleration values over a period of time (e.g., integrating acceleration values over a one-second period) using any of a variety of integration methods. In some embodiments, the sensor 100 performs at least some manipulations of the force signal and acceleration signal prior to transmitting the sensor data to the mechanical impedance generator 620, such as by generating velocity values based on the acceleration values. In some embodiments, the sensor 100 implements at least some functionality of the mechanical impedance generator 620.

The mechanical impedance generator 620 can maintain one or more models 624 that can be used to generate mechanical impedance values as well as other parameters based on the mechanical impedance values, and update the one or more models 624 responsive to the sensor data received from the sensor 100. The models 624 can include various machine learning models, such as supervised or unsupervised machine learning models.

The models 624 can include a calibration model 624. The calibration model 624 can include a transfer function that relates the voltage output of the sensor 100 (e.g., of the transducer 124) to a force sensitivity or the measured mechanical impedance. For example, the calibration model 624 can relate the force value and velocity value detected by the sensor 100 to the frequency at which the actuator 104 is driven.

The models 624 can include a finite element analysis (FEA) model 624. The FEA model 624 can maintain one or more parameters regarding the structure of the sensor 100 to determine the mechanical impedance. For example, the FEA model 624 can use any of a variety of parameters such as size dimensions and a mass of the transducer 124, a spring constant associated with the sensor 100, a damping constant (e.g., dashpot) associated with the sensor 100, and a mass of the load, among others. The FEA model 624 can indicate that the voltage output of the transducer 124 can decrease as a function of frequency at relatively low frequencies (while being affected primarily by the spring constant), remain constant at relatively middle frequencies (while being affected primarily by the damping constant), and increasing at relatively high frequencies (while being affected primarily by the mass of the transducer 124). The FEA model 624 can be validated or updated using the sensor data received from the sensor 100.

The models 624 can include one or more models, such as machine learning models, that can use as inputs various parameters (which may be measured or predetermined) such as temperature, pressure, hydration, humidity, skin conductance, to determine the mechanical impedance. By taking into account such parameters, the models 624 can more accurately determine the mechanical impedance.

In some embodiments, the models 624 maintain a baseline value for the mechanical impedance, or a baseline relationship between the input frequency and the resulting mechanical impedance. The models 624 can update the mechanical impedance using sensor data from the sensor 100. For example, the models 624 can maintain a user profile associated with a user of the sensor 100, and update the mechanical impedance for the user in the user profile using sensor data from the sensor 100.

The processing circuitry 616 can update, maintain, and selectively allow or prevent access to transmission of data associated with a user, including but not limited to eye tracking data, mechanical impedance data, user profile data, or various data associated with models 624. For example, the processing circuitry 616 may use as inputs, personal or biometric information of a user for user-authentication or experience-personalization purposes. A user may opt to make use of these functionalities, such as to enhance their experience using the system 600 or various devices associated with or in communication with one or more components of the system 600. As an example, a user may provide personal or biometric information to the system 600. The user's privacy settings may specify that such information may be used only for particular processes, such as authentication, and further specify that such information may not be shared with any third-party system or used for other processes or applications associated with the system 600 (or another system in communication with the system 600, such as a social network). The user's privacy setting may specify that data received or detected by the system 600, such as images, sensor data, eye tracking data, biometric data, or mechanical impedance data, may be used only for a limited purpose (e.g., authentication, operation of selected component(s) of the system 600), and further specify that such data may not be shared with any third-party system or used by other processes or applications associated with the system 600 or devices in communication with the system 600. The user's privacy setting may specify that the system 600 does not perform operations to detect (or store, or transmit) particular data, such as eye tracking data, unless the system 600 identifies that the privacy setting indicates permission to detect (or store, or transmit) the data.

The processing circuitry 616 can include an alert generator 628. The alert generator 628 can include any function, operation, routine, logic, or instructions to perform functions such as generating alerts regarding operation of haptic devices 636 or audio output devices 640 based on the mechanical impedance. For example, the alert generator 628 can generate alerts regarding conditions such as whether an HMD or other device implementing the haptic devices 636 or audio output devices 640 is properly fit or adjusted to a user. The alert generator 628 can compare the mechanical impedance to one or more thresholds, and output an alert responsive to the alert generator 628 meeting the one or more thresholds. The one or more thresholds may be predetermined thresholds indicative of an expected mechanical impedance given a particular frequency at which the actuator 104 of the sensor 100 is driven.

In some embodiments, the alert generator 628 updates the one or more thresholds using user feedback. For example, the alert generator 628 can request or receive feedback via a user interface of the HMD or other device implementing the sensor 100 indicating whether the sensor 100 is properly fit or adjusted to the user. The alert generator 628 can use the feedback as a labeled training data sample to train one or more machine learning models 624 to determine the thresholds (or adjust how the mechanical impedance generator 620 determines the mechanical impedance).

The processing circuitry 616 can include an output controller 632. The output controller 632 can include any function, operation, routine, logic, or instructions to perform functions such as controlling haptic devices 636, audio output devices 640, or sensor 100. The sensor 100 may be associated with or implemented by haptic devices 636 or audio output devices 640. The haptic devices 636 can include one or more actuators that can apply forces or vibrations to the user (e.g., using transducer 124 of sensor 100). The audio output devices 640 can include one or more speakers, transducers, or other devices that can generate audio (e.g., sound) output. The output controller 632 can cause the haptic devices 636 or audio output devices 640 to operate based on content to be delivered to the user (e.g., content received via simulation generator 644).

The output controller 632 can generate a control signal indicating one or more frequencies at which to drive the haptic devices 636, audio output devices 640, or sensor 100. For example, the output controller 632 can control the frequency at which the actuator 104 of the sensor 100 operates in order to measure mechanical impedance.

In some embodiments, the output controller 632 generates the control signal using the mechanical impedance determined by the mechanical impedance generator 620. For example, the output controller 632 can adjust a frequency, amplitude, intermittency, or other aspects of the control signal based on the mechanical impedance. The output controller 632 can compare the mechanical impedance to an expected mechanical impedance, and adjust the control signal based on the comparison.

In some embodiments, the output controller 632 controls a power usage responsive to the mechanical impedance. For example, if the mechanical impedance indicates that a device (e.g., HMD, wearable device) associated with the sensor 100 is not in use, the output controller 632 can reduce a power usage by or turn off the haptic devices 636 or the audio output devices 640. The output controller 632 can monitor the mechanical impedance (e.g., for a threshold duration of time), and reduce the power usage responsive to the mechanical impedance meeting a power usage criteria (e.g., the mechanical impedance indicates the load 150 has zero mass).

The output controller 632 can drive the sensor 100 together with at least one of the haptic device 636 or the audio output device 640. For example, the output controller 632 can use the transducer 124 of the sensor 100 as a relatively high frequency output device while also driving the haptic device 636 or the audio output device 640. This may allow for more effective tuning of the audio output components of the system 600. For example, capacitors or other power supply components of the system 600 may deliver power primarily based on current at certain frequencies (e.g., low frequencies) and voltage at other frequencies (e.g., high frequencies). By using the sensor 100 to deliver high frequency content, the output controller 632 can enable more effective usage of the power supply.

The processing circuitry 616 can include a simulation generator 644. The simulation generator 644 can include any function, operation, routine, logic, or instructions to perform functions such as operating an application, such as a game, trainer, or simulator, receive user input data, update the operation of the application based on the user input data, and provide display data to the image renderer 648 to enable the image renderer 648 to render display images for displaying the virtual environment. The simulation generator 644 can receive sensor data from the sensors 104 or the sensor 100, such as data regarding movement of the head or hands of the user, process the sensor data or motion data to identify the user input data, and update the operation of the application based on the identified user input data. For example, the simulation generator 644 can detect a movement of a hand of the user, such as a swing, push, or pull, and use the movement as a user input for the application. The simulation generator 644 can generate audio content and provide the audio content to the output controller 632 in order for the output controller 632 to drive the haptic devices 636 or audio output devices 640. The simulation generator 644 can generate depth buffer information corresponding to display data, enabling the image renderer 648 to render 3D image data.

The processing circuitry 616 can include an image renderer 648. The image renderer 648 can be a 3D image renderer. The image renderer 648 may use image related input data to process, generate and render display or presentation images to display or present on one or more display devices, such as via an HMD. The image renderer 648 can generate or create 2D images of a scene or view for display on display 652 and representing the scene or view in a 3D manner. The image renderer 648 can generate images for display on display 164 based on display data received from the simulation generator 644 (e.g., depth buffers received from the simulation generator 644). The display or presentation data to be rendered can include geometric models of 3D objects in the scene or view. The image renderer 648 may determine, compute or calculate the pixel values of the display or image data to be rendered to provide the desired or predetermined 3D image(s), such as 3D display data for the images 612 captured by the sensor 604.

The image renderer 648 can render frames of display data to one or more displays 652 based on temporal and/or spatial parameters. The image renderer 648 can render frames of image data sequentially in time, such as corresponding to times at which images are captured by the sensors 604 or at which frames of display data are received from simulation generator 644. The image renderer 648 can render frames of display data based on changes in position and/or orientation, such as the position and orientation of the HMD as indicated by sensors 604. The image renderer 648 can render frames of display data based on left-eye view(s) and right-eye view(s) such as displaying a left-eye view followed by a right-eye view or vice-versa.

The image renderer 648 can generate the display images using motion data regarding movement of the sensors 604. For example, the sensors 604 may change in at least one of position or orientation due to movement of a head of the user wearing an HMD that includes the sensors 604 (e.g., as described with reference to HMD system 700 of FIG. 7). The processing circuitry 616 can receive the sensor data from a position sensor (e.g., position sensor 720 described with reference to FIG. 7).

Although the image renderer 648 is shown as part of the processing circuitry 616, the image renderer may be formed as part of other processing circuitry of a separate device or component, such as the display device, for example within the HMD.

The system 600 can include one or more displays 652. The one or more displays 652 can be any type and form of electronic visual display. The displays may have or be selected with a predetermined resolution and refresh rate and size. The one or more displays can be of any type of technology such as LCD, LED, ELED or OLED based displays. The form factor of the one or more displays may be such to fit within the HMD as glasses or goggles in which the display(s) are the leans within the frame of the glasses or goggles. The displays 652 may have a refresh rate the same or different than a rate of refresh or frame rate of the processing circuitry 616 or the image renderer 648, the simulation generator 644, or the sensors 604.

Referring now to FIG. 7, in some implementations, an HMD system 700 can be used to implement the system 100. The HMD system 700 can include an HMD body 702, a left sensor 104a (e.g., left image capture device), a right sensor 104b (e.g., right image capture device), and the display 164. The HMD body 702 can have various form factors, such as glasses or a headset. The sensors 104a, 104b can be mounted to or integrated in the HMD body 702. The left sensor 104a can capture first images corresponding to a first view (e.g., left eye view), and the right sensor 104b can capture images corresponding to a second view (e.g., right eye view). In some embodiments, the HMD system 700 does not include image capture devices. The HMD system 700 can be used to implement VR functionality, such as to present a virtual environment via the display 164.

The HMD system 700 can include a top sensor 104c (e.g., top image capture device). The top sensor 104c can capture images corresponding to a third view different than the first view or the second view. For example, the top sensor 104c can be positioned between the left sensor 104a and right sensor 104b and above a baseline between the left sensor 104a and right sensor 104b. This can enable the top sensor 104c to capture images with depth information that may not be readily available to be extracted from the images captured by the left and right sensors 104a, 104b. For example, it may be difficult for depth information to be effectively extracted from images captured by the left and right sensors 104a, 104b in which edges (e.g., an edge of a table) are parallel to a baseline between the left and right sensors 104a, 104b. The top sensor 104c, being spaced from the baseline, can capture the third image to have a different perspective, and thus enable different depth information to be extracted from the third image, than the left and right sensors 104a, 104b.

The HMD system 700 can include processing circuitry 116, which can perform at least some of the functions described with reference to FIG. 1, including receiving sensor data from position sensors 104 (e.g., head tracking sensors) to detection movement of the HMD and generate warnings regarding potential collisions with obstacles based on the movement of the HMD.

The HMD system 700 can include communications circuitry 704. The communications circuitry 704 can be used to transmit electronic communication signals to and receive electronic communication signals from at least one of a client device 708 or a server 712. The communications circuitry 704 can include wired or wireless interfaces (e.g., jacks, antennas, transmitters, receivers, transceivers, wire terminals) for conducting data communications with various systems, devices, or networks. For example, the communications circuitry 704 can include an Ethernet card and port for sending and receiving data via an Ethernet-based communications network. The communications circuitry 704 can communicate via local area networks (e.g., a building LAN), wide area networks (e.g., the Internet, a cellular network), and/or conduct direct communications (e.g., NFC, Bluetooth). The communications circuitry 704 can conduct wired and/or wireless communications. For example, the communications circuitry 704 can include one or more wireless transceivers (e.g., a Wi-Fi transceiver, a Bluetooth transceiver, a NFC transceiver, a cellular transceiver). For example, the communications circuitry 704 can establish wired or wireless connections with the at least one of the client device 708 or the server 712. The communications circuitry 704 can establish a USB connection with the client device 708.

The HMD system 700 can be deployed using different architectures. In some embodiments, the HMD (e.g., HMD body 702 and components attached to the HMD body 702) comprises the processing circuitry 116 and is self-contained portable unit. In some embodiments, the HMD has portions of the processing circuitry 116 that work in cooperation with or in conjunction with any type of portable or mobile computing device or companion device that has the processing circuitry or portions thereof, such as in the form of a staging device, a mobile phone or wearable computing device. In some embodiments, the HMD has portions of the processing circuitry 116 that work in cooperation with or in conjunction with processing circuitry, or portions thereof, of a desktop computing device. In some embodiments, the HMD has portions of the processing circuitry 116 that works in cooperation with or in conjunction with processing circuitry, or portions thereof, of a server computing device, which may be deployed remotely in a data center or cloud computing environment. In any of the above embodiments, the HMD or any computing device working in conjunction with the HMD may communicate with one or more servers in performing any of the functionality and operations described herein.

The client device 708 can be any type and form of general purpose or special purpose computing device in any form factor, such as a mobile or portable device (phone, tablet, laptop, etc.), or a desktop or personal computing (PC) device. In some embodiments, the client device can be a special purpose device, such as in the form of a staging device, which may have the processing circuitry or portions thereof. The special purpose device may be designed to be carried by the user while wearing the HMD, such as by attaching the client device 708 to clothing or the body via any type and form of accessory attachment. The client device 708 may be used to perform any portion of the image and rendering processing pipeline described in connection with FIGS. 1 and 3. The HMD may perform some or other portions of the image and rendering processing pipeline such as generating display images of a virtual environment and rendering the display images to the display 164. The HMD can transmit and receive data with the client device 708 to leverage the client device 708's computing power and resources which may have higher specifications than those of the HMD.

The server 712 can be any type of form of computing device that provides applications, functionality or services to one or more client devices 708 or other devices acting as clients. In some embodiments, the server 712 can be a client device 708. The server 712 can be deployed in a data center or cloud computing environment accessible via one or more networks. The HMD and/or client device 708 can use and leverage the computing power and resources of the server 712. The HMD and/or client device 708 can implement any portion of the image and rendering processing pipeline described in connection with FIGS. 1 and 3. The server 712 can implement any portion of the image and rendering processing pipeline described in connection with FIGS. 1 and 3, and in some cases, any portions of the image and rendering processing pipeline not performed by client device 708 or HMD. The server 712 may be used to update the HMD and/or client device 708 with any updated to the applications, software, executable instructions and/or data on the HMD and/or client device 708.

The system 700 can include a position sensor 720. The position sensor 720 can output at least one of a position or an orientation of the body 702. As the image capture devices 104a, 104b, 104c can be fixed to the body 702 (e.g., at predetermined locations relative to the position sensor 720), the position sensor 720 can output at least one of a position or an orientation of each sensor 104a, 104b, 104c, which can be used for depth mapping of obstacles detected via the image capture devices 104a, 104b, 104c. The position sensor 720 can include at least one of an inertial measurement unit (IMU), an accelerometer, a gyroscope, or a magnetometer (e.g., magnetic compass).

The system 700 can include at least one hand device 724. The hand device 724 can be sized and shaped to be held by one or more hands of a user. The hand device 724 can operate as a user control device; for example, the hand device 724 can include various user interface elements (e.g., buttons, switches, toggles, etc.) that can be manipulated by a user to generate user inputs. For example, the hand device 724 can be used as a controller for interacting with a virtual environment being presented via the display 164 based on operation of an application by the HMD system 700. The hand device 724 can communicate with the communications circuitry 704, client device 708, and/or server 712 using various wired or wireless connections. The hand device 724 can include one or more position sensors 728, which can be similar to the position sensor 720. For example, the position sensor 728 can include at least one of an inertial measurement unit (IMU), an accelerometer, a gyroscope, or a magnetometer (e.g., magnetic compass), which can output sensor data including at least one of a position, a velocity, an acceleration, or an orientation of the hand device 724 in order for processing circuitry 116 to use the sensor data to detect movement of one or more hands of the user to determine whether to generate warnings regarding potential collisions between the one or more hands of the user and obstacles in a real world environment around the HMD 700.

Figure 8:
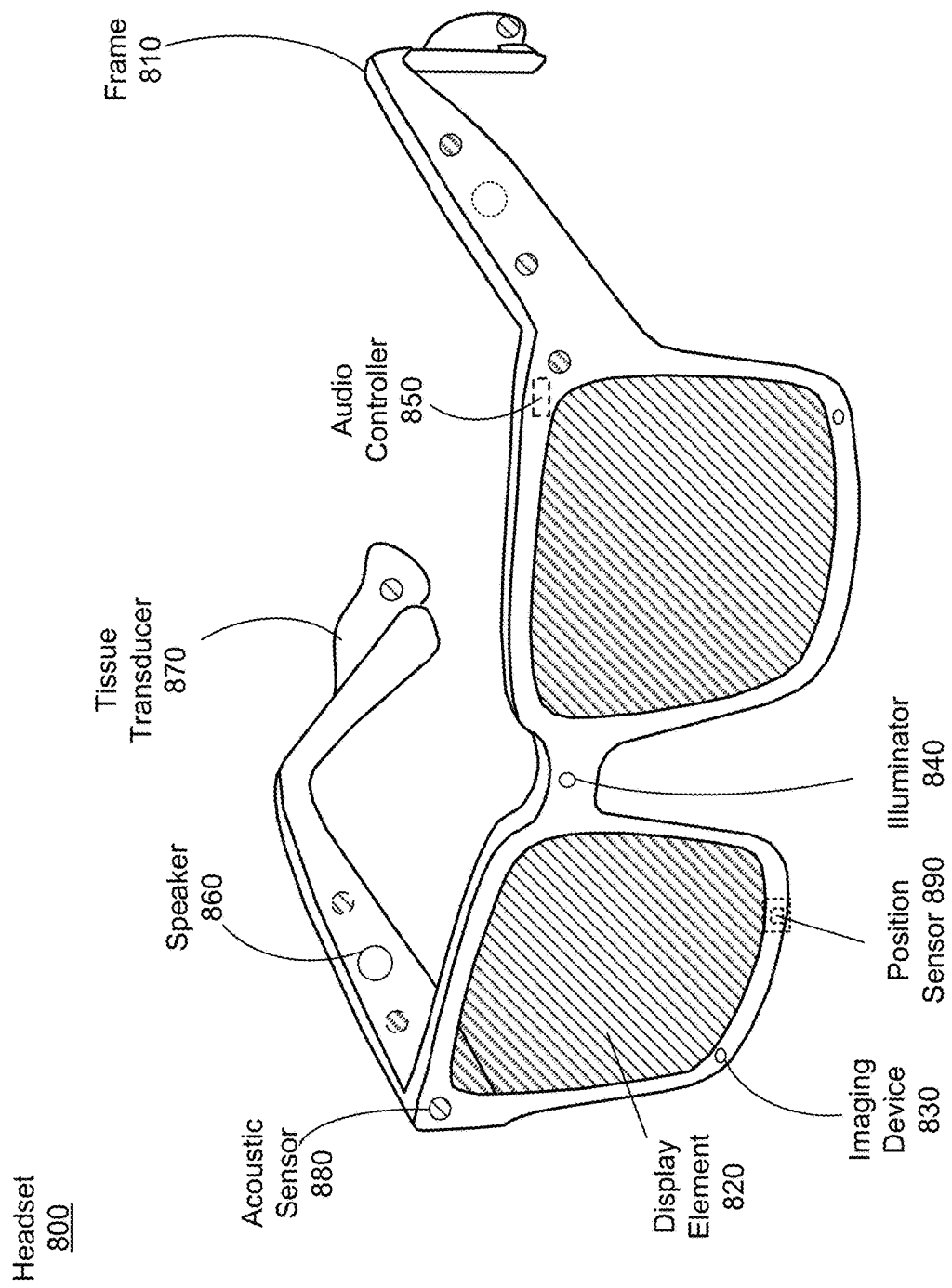
FIG. 8 is a perspective view of a headset implemented as an eyewear device according to an implementation of the present disclosure.

Referring now to FIG. 8, a headset 800 can be implemented as an eyewear device. In some embodiments, the eyewear device is a near eye display (NED). The headset 800 may be worn on the face of a user such that content (e.g., media content) is presented using a display assembly and/or an audio system. Examples of media content presented by the headset 800 include one or more images, video, audio, or some combination thereof. The headset 800 includes a frame, and may include, among other components, a display assembly including one or more display elements 820, a depth camera assembly (DCA), an audio system, and a position sensor 890. While FIG. 8 illustrates the components of the headset 800 in example locations on the headset 800, the components may be located elsewhere on the headset 800, on a peripheral device paired with the headset 800, or some combination thereof.

The frame 810 holds the other components of the headset 800. The frame 810 includes a front part that holds the one or more display elements 820 and end pieces (e.g., temples) to attach to a head of the user. The front part of the frame 810 bridges the top of a nose of the user. The length of the end pieces may be adjustable (e.g., adjustable temple length) to fit different users. The end pieces may also include a portion that curls behind the ear of the user (e.g., temple tip, ear piece).

The one or more display elements 820 provide light to a user wearing the headset 800. As illustrated the headset includes a display element 820 for each eye of a user. In some embodiments, a display element 820 generates image light that is provided to an eyebox of the headset 800. The eyebox is a location in space that an eye of user occupies while wearing the headset 800. For example, a display element 820 may be a waveguide display. A waveguide display includes a light source (e.g., a two-dimensional source, one or more line sources, one or more point sources, etc.) and one or more waveguides. Light from the light source is in-coupled into the one or more waveguides which outputs the light in a manner such that there is pupil replication in an eyebox of the headset 800. In-coupling and/or outcoupling of light from the one or more waveguides may be done using one or more diffraction gratings. In some embodiments, the waveguide display includes a scanning element (e.g., waveguide, mirror, etc.) that scans light from the light source as it is in-coupled into the one or more waveguides. One or both of the display elements 820 may be opaque and not transmit light from a local area around the headset 800. The local area is the area surrounding the headset 800. For example, the local area may be a room that a user wearing the headset 800 is inside, or the user wearing the headset 800 may be outside and the local area is an outside area. One or both of the display elements 820 can be at least partially transparent, such that light from the local area may be combined with light from the one or more display elements to produce AR content.

The display element 820 may include an additional optics block (not shown). The optics block may include one or more optical elements (e.g., lens, Fresnel lens, etc.) that direct light from the display element 820 to the eyebox. The optics block may, e.g., correct for aberrations in some or all of the image content, magnify some or all of the image, or some combination thereof.

The DCA determines depth information for a portion of a local area surrounding the headset 800. The DCA includes one or more imaging devices 830 and a DCA controller (not shown in FIG. 8), and may also include an illuminator 840. In some embodiments, the illuminator 840 illuminates a portion of the local area with light. The light may be, e.g., structured light (e.g., dot pattern, bars, etc.) in the infrared (IR), IR flash for time-of-flight, etc. In some embodiments, the one or more imaging devices 830 capture images of the portion of the local area that include the light from the illuminator 840.

The DCA controller computes depth information for the portion of the local area using the captured images and one or more depth determination techniques. The depth determination technique may be, e.g., direct time-of-flight (ToF) depth sensing, indirect ToF depth sensing, structured light, passive stereo analysis, active stereo analysis (uses texture added to the scene by light from the illuminator 840), some other technique to determine depth of a scene, or some combination thereof.

The audio system provides audio content. The audio system includes a transducer array, a sensor array, and an audio controller 850. Functionality described with reference to the components of the audio system can be distributed among the components in a different manner than is described here. For example, some or all of the functions of the controller may be performed by a remote server.

The transducer array presents sound to user. The transducer array includes a plurality of transducers. A transducer may be a speaker 860 or a tissue transducer 870 (e.g., a bone conduction transducer or a cartilage conduction transducer). Although the speakers 860 are shown exterior to the frame 810, the speakers 860 may be enclosed in the frame 810. In some embodiments, instead of individual speakers for each ear, the headset 800 includes a speaker array comprising multiple speakers integrated into the frame 810 to improve directionality of presented audio content. The tissue transducer 870 couples to the head of the user and directly vibrates tissue (e.g., bone or cartilage) of the user to generate sound.

The sensor array detects sounds within the local area of the headset 800. The sensor array includes a plurality of acoustic sensors 880. An acoustic sensor 880 captures sounds emitted from one or more sound sources in the local area (e.g., a room). Each acoustic sensor is configured to detect sound and convert the detected sound into an electronic format (analog or digital). The acoustic sensors 880 may be acoustic wave sensors, microphones, sound transducers, or similar sensors that are suitable for detecting sounds.

In some embodiments, one or more acoustic sensors 880 may be placed in an ear canal of each ear (e.g., acting as binaural microphones). In some embodiments, the acoustic sensors 880 may be placed on an exterior surface of the headset 800, placed on an interior surface of the headset 800, separate from the headset 800 (e.g., part of some other device), or some combination thereof. The number of acoustic detection locations may be increased to increase the amount of audio information collected and the sensitivity and/or accuracy of the information. The acoustic detection locations may be oriented such that the microphone is able to detect sounds in a wide range of directions surrounding the user wearing the headset 800.

The audio controller 850 processes information from the sensor array that describes sounds detected by the sensor array. The audio controller 850 may comprise a processor and a computer-readable storage medium. The audio controller 850 may be configured to generate direction of arrival (DOA) estimates, generate acoustic transfer functions (e.g., array transfer functions and/or head-related transfer functions), track the location of sound sources, form beams in the direction of sound sources, classify sound sources, generate sound filters for the speakers 860, or some combination thereof.

The position sensor 890 generates one or more measurement signals in response to motion of the headset 800. The position sensor 890 may be located on a portion of the frame 810 of the headset 800. The position sensor 890 may include an inertial measurement unit (IMU). Examples of position sensor 890 include: one or more accelerometers, one or more gyroscopes, one or more magnetometers, another suitable type of sensor that detects motion, a type of sensor used for error correction of the IMU, or some combination thereof. The position sensor 890 may be located external to the IMU, internal to the IMU, or some combination thereof.

In some embodiments, the headset 800 may provide for simultaneous localization and mapping (SLAM) for a position of the headset 800 and updating of a model of the local area. For example, the headset 800 may include a passive camera assembly (PCA) that generates color image data. The PCA may include one or more RGB cameras that capture images of some or all of the local area. In some embodiments, some or all of the imaging devices 830 of the DCA may also function as the PCA. The images captured by the PCA and the depth information determined by the DCA may be used to determine parameters of the local area, generate a model of the local area, update a model of the local area, or some combination thereof. Furthermore, the position sensor 890 tracks the position (e.g., location and pose) of the headset 100 within the room.

Figure 9:
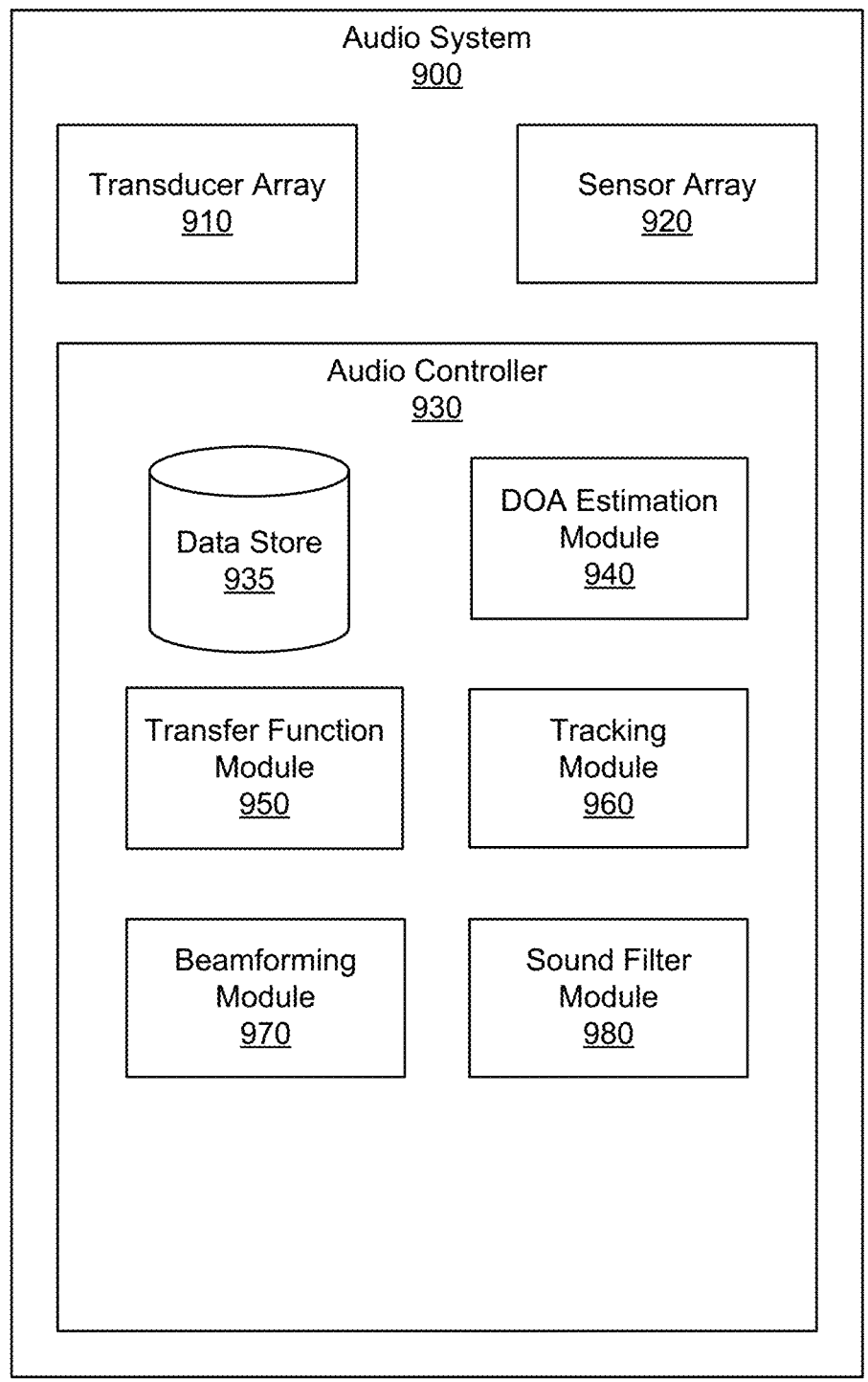
FIG. 9 is a block diagram of an audio system according to an implementation of the present disclosure.

Referring now to FIG. 9, an audio system 900 generates one or more acoustic transfer functions for a user. The audio system 900 may then use the one or more acoustic transfer functions to generate audio content for the user. The audio system 900 can include a transducer array 910, a sensor array 920, and an audio controller 930.

The transducer array 910 can configured to present audio content. The transducer array 910 includes a plurality of transducers, such as a speaker (e.g., the speaker 860), a tissue transducer (e.g., the tissue transducer 870), some other device that provides audio content, or some combination thereof. A tissue transducer may function as a bone conduction transducer or a cartilage conduction transducer. The transducer array 910 may present audio content via air conduction (e.g., via one or more speakers), via bone conduction (via one or more bone conduction transducer), via cartilage conduction audio system (via one or more cartilage conduction transducers), or some combination thereof. In some embodiments, the transducer array 910 may include one or more transducers to cover different parts of a frequency range. For example, a piezoelectric transducer may be used to cover a first part of a frequency range and a moving coil transducer may be used to cover a second part of a frequency range.

The bone conduction transducers can generate acoustic pressure waves by vibrating bone/tissue in the user's head. A bone conduction transducer may be coupled to a portion of a headset, and may be configured to be behind the auricle coupled to a portion of the user's skull. The bone conduction transducer receives vibration instructions from the audio controller 930, and vibrates a portion of the user's skull based on the received instructions. The vibrations from the bone conduction transducer generate a tissue-borne acoustic pressure wave that propagates toward the user's cochlea, bypassing the eardrum.

The cartilage conduction transducers generate acoustic pressure waves by vibrating one or more portions of the auricular cartilage of the ears of the user. A cartilage conduction transducer may be coupled to a portion of a headset, and may be configured to be coupled to one or more portions of the auricular cartilage of the ear. For example, the cartilage conduction transducer may couple to the back of an auricle of the ear of the user. The cartilage conduction transducer may be located anywhere along the auricular cartilage around the outer ear (e.g., the pinna, the tragus, some other portion of the auricular cartilage, or some combination thereof). Vibrating the one or more portions of auricular cartilage may generate: airborne acoustic pressure waves outside the ear canal; tissue born acoustic pressure waves that cause some portions of the ear canal to vibrate thereby generating an airborne acoustic pressure wave within the ear canal; or some combination thereof. The generated airborne acoustic pressure waves propagate down the ear canal toward the ear drum.

The transducer array 910 can generate audio content in accordance with instructions from the audio controller 930. In some embodiments, the audio content is spatialized. Spatialized audio content can appear to originate from a particular direction and/or target region (e.g., an object in the local area and/or a virtual object). For example, spatialized audio content can make it appear that sound is originating from a virtual singer across a room from a user of the audio system 900. The transducer array 910 may be coupled to a wearable device. The transducer array 910 may be a plurality of speakers that are separate from the wearable device (e.g., coupled to an external console).

The sensor array 920 can detect sounds within a local area surrounding the sensor array 920. The sensor array 920 may include a plurality of acoustic sensors that each detect air pressure variations of a sound wave and convert the detected sounds into an electronic format (analog or digital). The plurality of acoustic sensors may be positioned on a headset (e.g., headset 800), on a user (e.g., in an ear canal of the user), on a neckband, or some combination thereof. An acoustic sensor may be, e.g., a microphone, a vibration sensor, an accelerometer, or any combination thereof. In some embodiments, the sensor array 920 is configured to monitor the audio content generated by the transducer array 910 using at least some of the plurality of acoustic sensors. Increasing the number of sensors may improve the accuracy of information (e.g., directionality) describing a sound field produced by the transducer array 910 and/or sound from the local area.

The audio controller 930 controls operation of the audio system 900. The audio controller 930 can include a data store 935, a DOA estimator 940, a transfer function 950, a tracker 960, a beamformer 970, and a sound filter 980. The audio controller 930 may be located inside a headset, in some embodiments. Some embodiments of the audio controller 930 have different components than those described here. Similarly, functions can be distributed among the components in different manners than described here. For example, some functions of the controller may be performed external to the headset.

The data store 935 can store data for use by the audio system 900. Data in the data store 935 may include sounds recorded in the local area of the audio system 900, audio content, head-related transfer functions (HRTFs), transfer functions for one or more sensors, array transfer functions (ATFs) for one or more of the acoustic sensors, sound source locations, virtual model of local area, direction of arrival estimates, sound filters, and other data relevant for use by the audio system 900, or any combination thereof.

The DOA estimator 940 can localize sound sources in the local area based in part on information from the sensor array 920. Localization is a process of determining where sound sources are located relative to the user of the audio system 900. The DOA estimator 940 performs a DOA analysis to localize one or more sound sources within the local area. The DOA analysis may include analyzing the intensity, spectra, and/or arrival time of each sound at the sensor array 920 to determine the direction from which the sounds originated. In some cases, the DOA analysis may include any suitable algorithm for analyzing a surrounding acoustic environment in which the audio system 900 is located.

For example, the DOA analysis may be designed to receive input signals from the sensor array 920 and apply digital signal processing algorithms to the input signals to estimate a direction of arrival. These algorithms may include, for example, delay and sum algorithms where the input signal is sampled, and the resulting weighted and delayed versions of the sampled signal are averaged together to determine a DOA. A least mean squared (LMS) algorithm may also be implemented to create an adaptive filter. This adaptive filter may then be used to identify differences in signal intensity, for example, or differences in time of arrival. These differences may then be used to estimate the DOA. The DOA may be determined by converting the input signals into the frequency domain and selecting specific bins within the time-frequency (TF) domain to process. Each selected TF bin may be processed to determine whether that bin includes a portion of the audio spectrum with a direct path audio signal. Those bins having a portion of the direct-path signal may then be analyzed to identify the angle at which the sensor array 920 received the direct-path audio signal. The determined angle may then be used to identify the DOA for the received input signal. Other algorithms not listed above may also be used alone or in combination with the above algorithms to determine DOA.

The DOA estimator 940 may determine the DOA with respect to an absolute position of the audio system 900 within the local area. The position of the sensor array 920 may be received from an external system (e.g., some other component of a headset, an artificial reality console, a mapping server, a position sensor (e.g., the position sensor 190), etc.). The external system may create a virtual model of the local area, in which the local area and the position of the audio system 900 are mapped. The received position information may include a location and/or an orientation of some or all of the audio system 900 (e.g., of the sensor array 920). The DOA estimator 940 may update the estimated DOA based on the received position information.

The transfer function 950 can generate one or more acoustic transfer functions. Generally, a transfer function is a mathematical function giving a corresponding output value for each possible input value. Based on parameters of the detected sounds, the transfer function 950 generates one or more acoustic transfer functions associated with the audio system. The acoustic transfer functions may be array transfer functions (ATFs), head-related transfer functions (HRTFs), other types of acoustic transfer functions, or some combination thereof. An ATF characterizes how the microphone receives a sound from a point in space.

An ATF can include a number of transfer functions that characterize a relationship between the sound source and the corresponding sound received by the acoustic sensors in the sensor array 920. Accordingly, for a sound source there is a corresponding transfer function for each of the acoustic sensors in the sensor array 920. The sound source may be, e.g., someone or something generating sound in the local area, the user, or one or more transducers of the transducer array 910. The ATF for a particular sound source location relative to the sensor array 920 may differ from user to user due to a person's anatomy (e.g., ear shape, shoulders, etc.) that affects the sound as it travels to the person's ears. Accordingly, the ATFs of the sensor array 920 can be personalized for each user of the audio system 900.

The transfer function 950 can determine one or more HRTFs for a user of the audio system 900. The HRTF can characterize how an ear receives a sound from a point in space. The HRTF for a particular source location relative to a person can be unique to each ear of the person (and is unique to the person) due to the person's anatomy (e.g., ear shape, shoulders, etc.) that affects the sound as it travels to the person's ears. In some embodiments, the transfer function 950 may determine HRTFs for the user using a calibration process. In some embodiments, the transfer function 950 may provide information about the user to a remote system. The remote system determines a set of HRTFs that are customized to the user using, e.g., machine learning, and provides the customized set of HRTFs to the audio system 900.

The tracker 960 can track locations of one or more sound sources. The tracker 960 may compare current DOA estimates and compare them with a stored history of previous DOA estimates. In some embodiments, the audio system 900 may recalculate DOA estimates on a periodic schedule, such as once per second, or once per millisecond. The tracking module may compare the current DOA estimates with previous DOA estimates, and in response to a change in a DOA estimate for a sound source, the tracker 960 may determine that the sound source moved. In some embodiments, the tracker 960 may detect a change in location based on visual information received from the headset or some other external source. The tracker 960 may track the movement of one or more sound sources over time. The tracker 960 may store values for a number of sound sources and a location of each sound source at each point in time. In response to a change in a value of the number or locations of the sound sources, the tracker 960 may determine that a sound source moved. The tracker 960 may calculate an estimate of the localization variance. The localization variance may be used as a confidence level for each determination of a change in movement.

The beamformer 970 can process one or more ATFs to selectively emphasize sounds from sound sources within a certain area while de-emphasizing sounds from other areas. In analyzing sounds detected by the sensor array 920, the beamformer 970 may combine information from different acoustic sensors to emphasize sound associated from a particular region of the local area while deemphasizing sound that is from outside of the region. The beamformer 970 may isolate an audio signal associated with sound from a particular sound source from other sound sources in the local area based on, e.g., different DOA estimates from the DOA estimator 940 and the tracker 960. The beamformer 970 may thus selectively analyze discrete sound sources in the local area. In some embodiments, the beamformer 970 may enhance a signal from a sound source. For example, the beamformer 970 may apply sound filters which eliminate signals above, below, or between certain frequencies. Signal enhancement acts to enhance sounds associated with a given identified sound source relative to other sounds detected by the sensor array 920.

The sound filter 980 can determine sound filters for the transducer array 910. In some embodiments, the sound filters cause the audio content to be spatialized, such that the audio content appears to originate from a target region. The sound filter 980 may use HRTFs and/or acoustic parameters to generate the sound filters. The acoustic parameters describe acoustic properties of the local area. The acoustic parameters may include, e.g., a reverberation time, a reverberation level, a room impulse response, etc. In some embodiments, the sound filter 980 calculates one or more of the acoustic parameters. In some embodiments, the sound filter 980 requests the acoustic parameters from a mapping server (e.g., as described below with regard to FIG. YY).

The sound filter 980 can provide the sound filters to the transducer array 910. In some embodiments, the sound filters may cause positive or negative amplification of sounds as a function of frequency.

Figure 10:
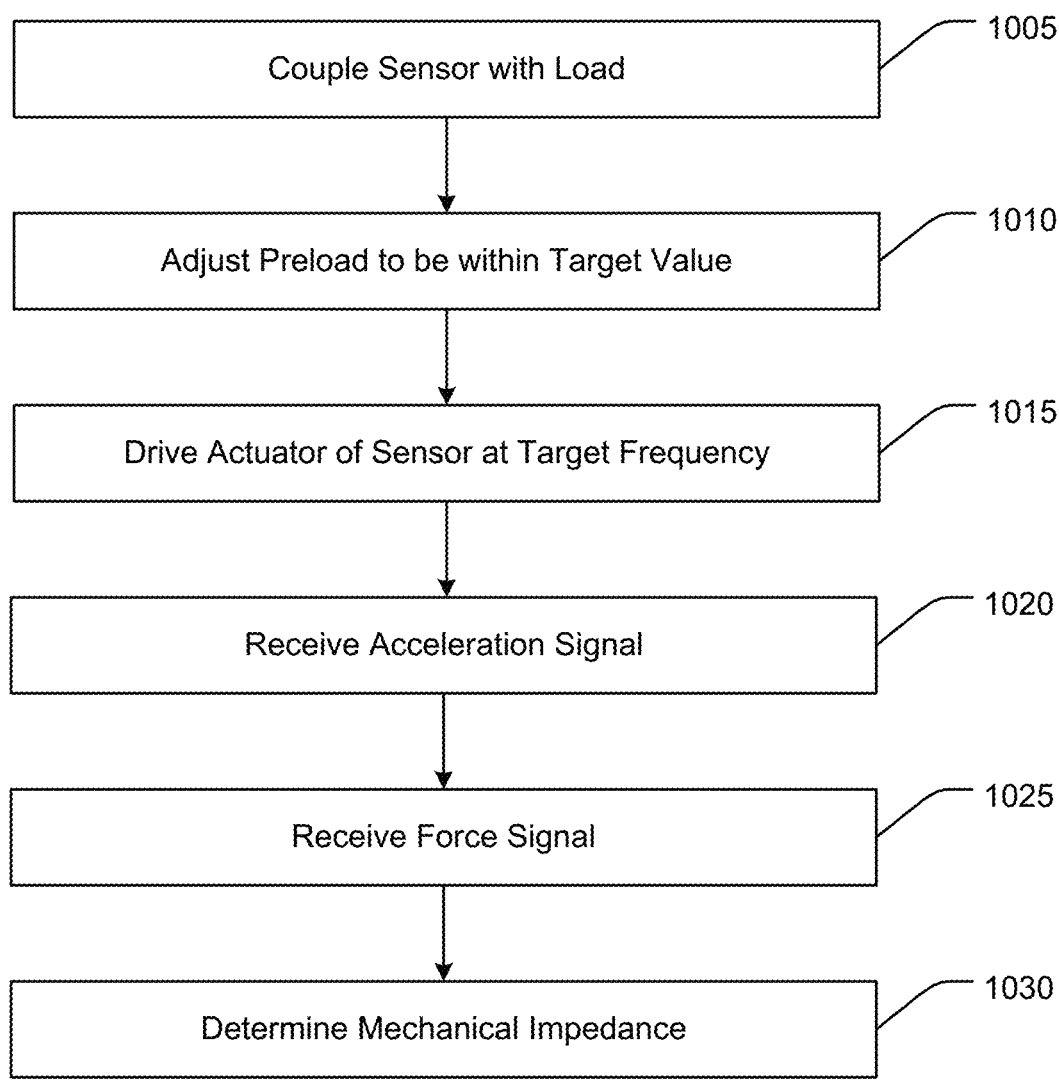
FIG. 10 is a flow diagram of a method for characterization of mechanical impedance of biological tissues according to an implementation of the present disclosure.

Referring now to FIG. 10, a method 1000 for characterizing mechanical impedance of biological tissues is illustrated. In some embodiments, the method 1000 can include one or more of the following operations which may or may not be performed in sequence. The method 1000 can include coupling a sensor to a load (1005). The method 1000 can include adjusting a preload to be within a target value (1010). The method 1000 can include driving an actuator of the sensor at a target frequency (1015). The method 1000 can include receiving an acceleration signal from an accelerometer coupled with the actuator (1020). The method 1000 can include receiving a force signal from a transducer of the sensor (1025). The method 1000 can include determining a mechanical impedance of the load using the acceleration signal and the force signal (1030). The method 1100 can be executed using various devices and systems described herein, including but not limited to the sensor 100 and the system 600.

In more detail, at 1005, a sensor is coupled to a load. The sensor can be positioned adjacent to the load. For example, a transducer of the sensor can be positioned in contact with the load. The transducer can include at least one piezoelectric layer that is contacted with the load or at least one bracket adjacent to the at least one piezoelectric layer that is contacted with the load. The transducer can have an internal mass less than a threshold mass (e.g., a threshold mass related to the load).

At 1010, a preload is adjusted to a value within a threshold of a target value (e.g., a target DC force value). The preload can indicate a constant or static force that the sensor applies to the load (e.g., separate from or in addition to the force applied responsive to operation of the actuator), such as a static force that the transducer applies to a tissue of the subject associated with the load. The preload can be monitored using a sensor, such as a DC force sensor. The preload can be adjusted by controlling a spring coupled to the load. For example, a length or shape of the spring can be adjusted (e.g., using an actuator) based on the monitored preload to increase or decrease the preload to be within the threshold of the target value. The target value may be associated with a value at which bone conduction or cartilage conduction can be performed effectively. The preload can be periodically monitored to enable periodic or continuous control of the preload, such as for maintaining the preload within the threshold of the target value while operating the sensor to determine the mechanical impedance.

At 1010, an actuator of the sensor is driven at a target frequency. The actuator can be driven responsive to receiving a control signal from a remote device, such as an HMD, wearable device, or remote server. The target frequency can be selected to facilitate measuring mechanical impedance of the load. The actuator can include a shaker, such as a high bandwidth shaker, that can oscillate at the target frequency responsive to receiving the control signal. The actuator can be driven periodically, according to a schedule, or otherwise responsive to the control signal.

At 1015, an acceleration signal is received from an accelerometer of the sensor. The acceleration signal can be received periodically or responsive to requesting the acceleration signal from the accelerometer. The acceleration signal can be outputted responsive to the acceleration meeting or exceeding a minimum threshold. The accelerometer can be coupled with the actuator to output the acceleration signal based on movement caused by the actuator. The acceleration signal can indicate an acceleration value or a velocity value generated by integrating the acceleration value over a duration of time.

At 1020, a force signal is received from the transducer. The force signal can include a voltage representative of a force measured by the transducer. The force signal can be received periodically, responsive to requesting the force signal, or responsive to the force value meeting or exceeding a threshold. The force signal can be generated by the transducer based on movement caused by the actuator being transferred to the transducer (and the load) via a rigid member.

At 1025, a mechanical impedance is determined using the force signal and the acceleration signal. For example, the mechanical impedance can be determined by dividing the force value by the velocity value. The mechanical impedance can be determined by providing the force signal and acceleration signal to one or more calibration models, FEA models, or machine learning models. The mechanical impedance can be determined responsive to receiving the force signal and the acceleration signal, on a periodic basis (e.g., every one second responsive to sampling the force signal and acceleration signal), or responsive to receiving a request for the mechanical impedance.

The method 1000 or steps or operations thereof can be performed based on various conditions. The method 1000 can be performed responsive to detecting that the HMD, AR system, or VR system is in an initialization, calibration, restart, or setup mode. In some embodiments, the method 1000 is performed on a periodic basis, such as to periodically detect mechanical impedance and modify operation of the system using the mechanical impedance. The method 1000 can be performed responsive to user input, such as user input indicating instructions to calibrate or re-calibrate the sensor.

Figure 11:
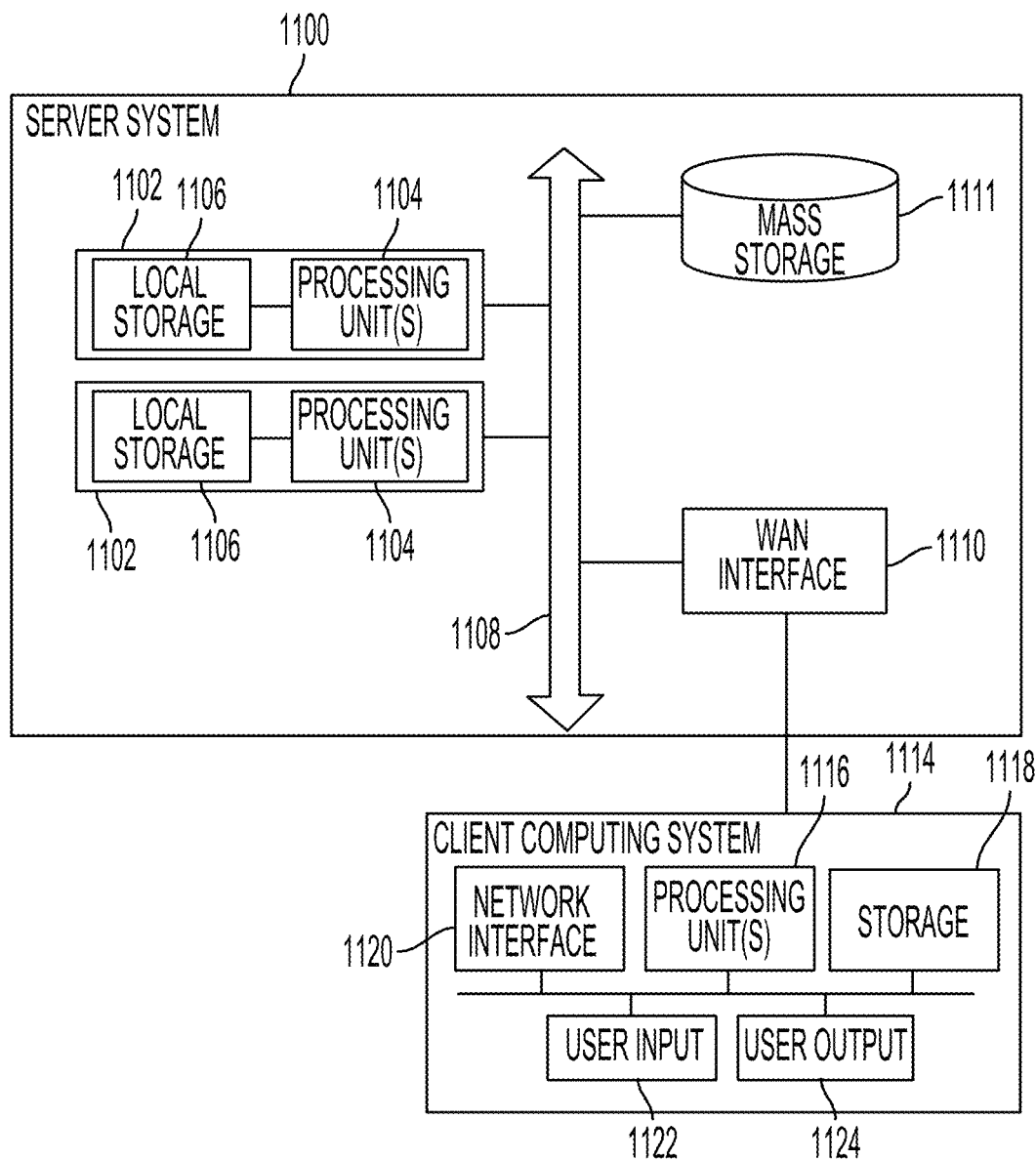
FIG. 11 is a block diagram of a computing environment according to an implementation of the present disclosure.

Various operations described herein can be implemented on computer systems. FIG. 11 shows a block diagram of a representative server system 1100 and client computer system 1114 usable to implement the present disclosure. Server system 1100 or similar systems can implement services or servers described herein or portions thereof. Client computer system 1114 or similar systems can implement clients described herein. Each of the systems 100, 600 and others described herein can incorporate features of the systems 1100, 1114.

Server system 1100 can have a modular design that incorporates a number of modules 1102 (e.g., blades in a blade server); while two modules 1102 are shown, any number can be provided. Each module 1102 can include processing unit(s) 1104 and local storage 1106.

Processing unit(s) 1104 can include a single processor, which can have one or more cores, or multiple processors. Processing unit(s) 1104 can include a general-purpose primary processor as well as one or more special-purpose co-processors such as graphics processors, digital signal processors, or the like. Some or all processing units 1104 can be implemented using customized circuits, such as application specific integrated circuits (ASICs) or field programmable gate arrays (FPGAs). Such integrated circuits execute instructions that are stored on the circuit itself. Processing unit(s) 1104 can execute instructions stored in local storage 1106. Any type of processors in any combination can be included in processing unit(s) 1104.

Local storage 1106 can include volatile storage media (e.g., conventional DRAM, SRAM, SDRAM, or the like) and/or non-volatile storage media (e.g., magnetic or optical disk, flash memory, or the like). Storage media incorporated in local storage 1106 can be fixed, removable or upgradeable as desired. Local storage 1106 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 1104 need at runtime. The ROM can store static data and instructions that are needed by processing unit(s) 1104. The permanent storage device can be a non-volatile read-and-write memory device that can store instructions and data even when module 1102 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

Local storage 1106 can store one or more software programs to be executed by processing unit(s) 1104, such as an operating system and/or programs implementing various server functions such as functions of the system 100, or any other system described herein, or any other server(s) associated with the system 100 or any other system described herein.

"Software" refers generally to sequences of instructions that, when executed by processing unit(s) 1104 cause server system 1100 (or portions thereof) to perform various operations, thus defining one or more specific machine implementations that execute and perform the operations of the software programs. The instructions can be stored as firmware residing in read-only memory and/or program code stored in non-volatile storage media that can be read into volatile working memory for execution by processing unit(s) 1104. Software can be implemented as a single program or a collection of separate programs or program modules that interact as desired. From local storage 1106 (or non-local storage described below), processing unit(s) 1104 can retrieve program instructions to execute and data to process in order to execute various operations described above.

In some server systems 1100, multiple modules 1102 can be interconnected via a bus or other interconnect 1108, forming a local area network that supports communication between modules 1102 and other components of server system 1100. Interconnect 1108 can be implemented using various technologies including server racks, hubs, routers, etc.

A wide area network (WAN) interface 1110 can provide data communication capability between the local area network (interconnect 1108) and a larger network, such as the Internet. Conventional or other activities technologies can be used, including wired (e.g., Ethernet, IEEE 802.3 standards) and/or wireless technologies (e.g., Wi-Fi, IEEE 802.11 standards).

Local storage 1106 can provide working memory for processing unit(s) 1104, providing fast access to programs and/or data to be processed while reducing traffic on interconnect 1108. Storage for larger quantities of data can be provided on the local area network by one or more mass storage subsystems 1112 that can be connected to interconnect 1108. Mass storage subsystem 1112 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 1112. Additional data storage resources may be accessible via WAN interface 1110 (potentially with increased latency).

Server system 1100 can operate in response to requests received via WAN interface 1110. For example, one of modules 1102 can implement a supervisory function and assign discrete tasks to other modules 1102 in response to received requests. Conventional work allocation techniques can be used. As requests are processed, results can be returned to the requester via WAN interface 1110. Such operation can generally be automated. WAN interface 1110 can connect multiple server systems 1100 to each other, providing scalable systems capable of managing high volumes of activity. Conventional or other techniques for managing server systems and server farms (collections of server systems that cooperate) can be used, including dynamic resource allocation and reallocation.

Server system 1100 can interact with various user-owned or user-operated devices via a wide-area network such as the Internet. An example of a user-operated device is shown in FIG. 4 as client computing system 1114. Client computing system 1114 can be implemented, for example, as a consumer device such as a smartphone, other mobile phone, tablet computer, wearable computing device (e.g., smart watch, eyeglasses), desktop computer, laptop computer, and so on.

For example, client computing system 1114 can communicate via WAN interface 1110. Client computing system 1114 can include conventional computer components such as processing unit(s) 1116, storage device 1118, network interface 1120, user input device 1122, and user output device 1124. Client computing system 1114 can be a computing device implemented in a variety of form factors, such as a desktop computer, laptop computer, tablet computer, smartphone, other mobile computing device, wearable computing device, or the like.

Processor 1116 and storage device 1118 can be similar to processing unit(s) 1104 and local storage 1106 described above. Suitable devices can be selected based on the demands to be placed on client computing system 1114; for example, client computing system 1114 can be implemented as a "thin" client with limited processing capability or as a high-powered computing device. Client computing system 1114 can be provisioned with program code executable by processing unit(s) 1116 to enable various interactions with server system 1100 of a message management service such as accessing messages, performing actions on messages, and other interactions described above. Some client computing systems 1114 can also interact with a messaging service independently of the message management service.

Network interface 1120 can provide a connection to a wide area network (e.g., the Internet) to which WAN interface 1110 of server system 1100 is also connected. Network interface 1120 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 1122 can include any device (or devices) via which a user can provide signals to client computing system 1114; client computing system 1114 can interpret the signals as indicative of particular user requests or information. User input device 1122 can include any or all of a keyboard, touch pad, touch screen, mouse or other pointing device, scroll wheel, click wheel, dial, button, switch, keypad, microphone, and so on.

User output device 1124 can include any device via which client computing system 1114 can provide information to a user. For example, user output device 1124 can include a display to display images generated by or delivered to client computing system 1114. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). A device such as a touchscreen that function as both input and output device can be used. Output devices 1124 can be provided in addition to or instead of a display. Examples include indicator lights, speakers, tactile "display" devices, printers, and so on.

Some implementations include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 1104 and 1116 can provide various functionality for server system 1100 and client computing system 1114, including any of the functionality described herein as being performed by a server or client, or other functionality associated with message management services.

It will be appreciated that server system 1100 and client computing system 1114 are illustrative and that variations and modifications are possible. Computer systems used in connection with the present disclosure can have other capabilities not specifically described here. Further, while server system 1100 and client computing system 1114 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Implementations of the present disclosure can be realized in a variety of apparatus including electronic devices implemented using any combination of circuitry and software.

Having now described some illustrative implementations, it is apparent that the foregoing is illustrative and not limiting, having been presented by way of example. In particular, although many of the examples presented herein involve specific combinations of method acts or system elements, those acts and those elements can be combined in other ways to accomplish the same objectives. Acts, elements and features discussed in connection with one implementation are not intended to be excluded from a similar role in other implementations or implementations.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular can also embrace implementations including a plurality of these elements, and any references in plural to any implementation or element or act herein can also embrace implementations including only a single element. References in the singular or plural form are not intended to limit the presently disclosed systems or methods, their components, acts, or elements to single or plural configurations. References to any act or element being based on any information, act or element can include implementations where the act or element is based at least in part on any information, act, or element.

Any implementation disclosed herein can be combined with any other implementation or embodiment, and references to "an implementation," "some implementations," "one implementation" or the like are not necessarily mutually exclusive and are intended to indicate that a particular feature, structure, or characteristic described in connection with the implementation can be included in at least one implementation or embodiment. Such terms as used herein are not necessarily all referring to the same implementation. Any implementation can be combined with any other implementation, inclusively or exclusively, in any manner consistent with the aspects and implementations disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Systems and methods described herein may be embodied in other specific forms without departing from the characteristics thereof. Further relative parallel, perpendicular, vertical or other positioning or orientation descriptions include variations within +/−10% or +/−10 degrees of pure vertical, parallel or perpendicular positioning. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining may be stationary (e.g., permanent or fixed) or moveable (e.g., removable or releasable). Such joining may be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References to "or" can be construed as inclusive so that any terms described using "or" can indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

References herein to the positions of elements (e.g., "top," "bottom," "above," "below") are merely used to describe the orientation of various elements in the FIGURES. The orientation of various elements may differ according to other exemplary embodiments, and that such variations are intended to be encompassed by the present disclosure.

What is claimed is:

1. A sensor system, comprising:
an actuator that generates motion;
an accelerometer coupled with the actuator, the accelerometer outputs an acceleration signal responsive to at least the motion of the actuator;
a rigid member extending from a first end coupled with the accelerometer to a second end;
a transducer coupled with the second end of the rigid member, the transducer configured to couple with a load such that the transducer is between the rigid member and the load, the transducer outputs a force signal responsive to at least a portion of the motion of the actuator transmitted to the transducer via the rigid member; and
one or more processors that determine a mechanical impedance of the load based at least on the acceleration signal and the force signal.

2. The sensor system of claim 1, wherein the actuator comprises a shaker that oscillates at a frequency in a frequency range that at least partially overlaps with a frequency range from 20 Hz to 20 kHz.

3. The sensor system of claim 1, wherein the rigid member has a rigidity greater than a threshold rigidity when oscillated at a frequency in a frequency range from 20 Hz to 20 kHz, the threshold rigidity is at least 500 Newtons/meter.

4. The sensor system of claim 1, wherein the one or more processors determine a calibration function using the acceleration signal and the force signal.

5. The sensor system of claim 1, wherein the one or more processors maintain a finite element analysis (FEA) model that relates the mechanical impedance to one or more parameters of at least the transducer.

6. The sensor system of claim 5, wherein the FEA model determines the mechanical impedance based on a frequency of operation of the actuator.

7. The sensor system of claim 1, wherein the one or more processors maintain a machine learning model that relates the mechanical impedance to one or more parameters of at least one of the transducer or the load.

8. The sensor system of claim 1, wherein the one or more processors update a user profile using the mechanical impedance.

9. The sensor system of claim 1, wherein the one or more processors compare the mechanical impedance to an expected mechanical impedance and output an alert responsive to the comparison.

10. The sensor system of claim 1, wherein the one or more processors control the actuator to cause the transducer to apply a desired output to the load, the desired output including at least one of a haptic output or an audio output.

11. The sensor system of claim 1, wherein the one or more processors:
   compare the mechanical impedance to a threshold impedance to determine an operational mode of a device that includes the transducer; and
   control a power usage of the device based at least on the operational mode.

12. The sensor system of claim 1, wherein the transducer comprises a plurality of piezoelectric layers.

13. The sensor system of claim 1, further comprising a pad coupled with the transducer to connect the transducer with the load.

14. The sensor system of claim 1, wherein the rigid member tapers to a tip at the second end of the rigid member.

15. The sensor system of claim 1, wherein the one or more processors drive the actuator at a first frequency and at least one of a haptic output device or an audio output device at a second frequency less than the first frequency.

16. The sensor system of claim 1, wherein the transducer outputs an AC component of the force signal, the sensor system further comprising a DC force sensor positioned between the transducer and the rigid member, the DC force sensor outputs a DC component of the force signal.

17. A method, comprising:
coupling a sensor with a load;
driving an actuator of the sensor at a target frequency;
receiving an acceleration signal from an accelerometer of the sensor;
receiving a force signal from a transducer of the sensor, the transducer between the load and a rigid member coupled with the actuator; and
determining, by one or more processors, a mechanical impedance of the load using the acceleration signal and the force signal.

18. The method of claim 17, further comprising controlling the actuator to cause the transducer to apply a desired output to the load, the desired output including at least one of a haptic output or an audio output.

19. The method of claim 17, further comprising applying a preload to the load.

20. A sensor, comprising:
an actuator that generates motion;
an accelerometer coupled with the actuator, the accelerometer outputs an acceleration signal responsive to at least the motion of the actuator;
a rigid member extending from a first end coupled with the accelerometer to a second end; and
a piezoelectric transducer coupled with the second end of the rigid member, the piezoelectric transducer configured to couple with a load such that the transducer is between the rigid member and the load, the piezoelectric transducer outputs a force signal responsive to at least a portion of the motion of the actuator transmitted to the piezoelectric transducer via the rigid member.

* * * * *